United States Patent
Lum et al.

(10) Patent No.: US 10,545,997 B2
(45) Date of Patent: *Jan. 28, 2020

(54) CONSENSUS SEQUENCE IDENTIFICATION

(71) Applicant: Ayasdi AI LLC, Menlo Park, CA (US)

(72) Inventors: Pek Yee Lum, Palo Alto, CA (US);
Eithon Cadag, Foster City, CA (US);
Johan Grahnen, Palo Alto, CA (US);
Joshua Lewis, San Francisco, CA (US);
Harlan Sexton, Palo Alto, CA (US)

(73) Assignee: Ayasdi AI LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,809

(22) Filed: Aug. 27, 2018

(65) Prior Publication Data

US 2019/0005114 A1    Jan. 3, 2019

Related U.S. Application Data

(63) Continuation of application No. 14/597,156, filed on Jan. 14, 2015, now Pat. No. 10,102,271.

(Continued)

(51) Int. Cl.
*G06F 16/28* (2019.01)
*G06F 16/955* (2019.01)
(Continued)

(52) U.S. Cl.
CPC .......... *G06F 16/285* (2019.01); *G06F 16/955* (2019.01); *G16H 10/60* (2018.01); *G16H 50/20* (2018.01); *G16H 50/70* (2018.01)

(58) Field of Classification Search
CPC .................................................... G06F 16/285
See application file for complete search history.

(56) References Cited

U.S. PATENT DOCUMENTS 6,295,504 B1    9/2001 Ye
6,526,405 B1 *  2/2003 Mannila ............... G06K 9/62
                                              707/999.004

(Continued)

FOREIGN PATENT DOCUMENTS

CN    102687138    9/2012
CN    103384887    11/2013

OTHER PUBLICATIONS

European Patent Application No. 15737570.0, Search Report dated Aug. 4, 2017.

(Continued)

*Primary Examiner* — Mohammad S Rostami
(74) *Attorney, Agent, or Firm* — Ahmann Kloke LLP

(57) ABSTRACT

An example method comprises receiving historical information of episodes, constructing event sets from the historical information, categorizing each event with general labels and synthetic labels, learning an event metric on the events by using the general and synthetic labels to perform dimensionality reduction to associate a vector with each event and to determine an angle between every two vectors, determining an event set metric using distances between each pair of event sets, deriving a sequence metric on the episodes, the sequence metric obtaining a preferred match between two episodes, deriving a subsequence metric on the episodes, the subsequence metric is a function of the event set metric on subsequences of each episode, grouping episodes into subgroups based on distances, for at least one subgroup, generating a consensus sequence by finding a preferred sequence of events, and the episodes of the subgroup, and generating a report indicating the consensus sequence.

22 Claims, 17 Drawing Sheets

Related U.S. Application Data

(60) Provisional application No. 61/964,800, filed on Jan. 14, 2014.

(51) Int. Cl.
  G16H 10/60 (2018.01)
  G16H 50/70 (2018.01)
  G16H 50/20 (2018.01)

(56) References Cited

U.S. PATENT DOCUMENTS

| | | |
|---|---|---|
| 6,865,582 B2 | 3/2005 | Obradovic |
| 6,986,035 B2 | 1/2006 | Stevens, Jr. |
| 7,869,658 B2 | 1/2011 | Blose |
| 8,713,021 B2 | 4/2014 | Bellegarda |
| 8,935,291 B2 | 1/2015 | Chen |
| 8,983,959 B2 | 3/2015 | Isaacson |
| 9,147,252 B2 | 9/2015 | Davis |
| 9,147,273 B1 | 9/2015 | Allen |
| 9,448,966 B2 | 9/2016 | Varakur |
| 9,465,857 B1 | 10/2016 | DeLand |
| 2003/0055614 A1 | 3/2003 | Pelikan |
| 2005/0010541 A1 | 1/2005 | Rietman |
| 2005/0076045 A1 | 4/2005 | Stenslet |
| 2009/0083075 A1 | 3/2009 | Henschke |
| 2009/0228830 A1 | 9/2009 | Herz |
| 2010/0161594 A1* | 6/2010 | Prasad ............ G06F 16/90335 707/722 |
| 2011/0161311 A1 | 6/2011 | Mishne |
| 2011/0197032 A1* | 8/2011 | Patey ............... G06F 16/24552 711/133 |
| 2012/0041772 A1 | 2/2012 | Ebadollahi |
| 2012/0059670 A1 | 3/2012 | Sanborn |
| 2012/0185518 A1* | 7/2012 | Giampaolo .......... H04L 9/3213 707/821 |
| 2012/0232930 A1* | 9/2012 | Schmidt ................ G06Q 10/10 705/3 |
| 2013/0325416 A1 | 12/2013 | Benbrahim |
| 2014/0218383 A1 | 8/2014 | Srivastava |
| 2014/0379473 A1 | 12/2014 | Zhou |
| 2016/0026706 A1 | 1/2016 | Lum |
| 2016/0071162 A1 | 3/2016 | Ogawa |

OTHER PUBLICATIONS

International Application No. PCT/US2015/011477, International Search Report and Written Opinion dated Jun. 3, 2015.

International Application No. PCT/US2017/022367, International Search Report and Written Opinion dated Jun. 12, 2017.

Wongsuphasawat, Krist et al., "Finding Comparable Temporal Categorical Records: A Similarity Measure with an Interactive Visualization," IEEE Symposium on Visual Analytics Science and Technology (VAST 2009), pp. 27-34, Oct. 12, 2009.

\* cited by examiner

|  | LAB | XR | ... | PAIN |
|---|---|---|---|---|
| LAB123 | 0.213 | 0.00012 | ... | 0.5 |
| ... | ... | ... | ... | ... |
| GENERIC LAB | 0.647 | 0.12 | ... | 0.01 |
| XR1107 | 0.476 | 0.066 | ... | 0.0003 |
| ... | ... | ... | ... | ... |

G1: LAB123, LAB665, LAB012, GENERIC XR

G2: LAB123, LAB665, LAB013, XR1107

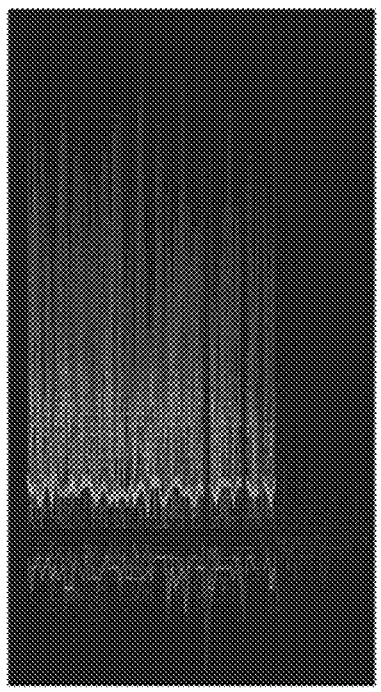

| Time (minutes relative to surgery) 902 | Parent Category 904 | Category 906 | Code 908 | Interval 910 | Description 912 |
|---|---|---|---|---|---|
| -17114 | Orders | EKG | EKG1 | unknown | EKG 12-LEAD |
| -17114 | Labs | LAB | LAB1725 | unknown | CBC WITH DIFFERENTIAL |
| -17114 | Labs | LAB | LAB276 | unknown | TYPE AND SCREEN |
| -17114 | Labs | LAB | LAB3038 | unknown | URINALYSIS WITH REFLEX CULTURE |
| -17114 | Labs | LAB | LAB15 | unknown | BASIC METABOLIC PANEL |
| -17114 | Labs | LAB | LAB347 | unknown | URINALYSIS |
| -17114 | Labs | LAB | LAB3338 | unknown | MRSA ACTIVE SURVEILLANCE |
| -17114 | Labs | LAB | LAB320 | unknown | PROTIME-INR |
| -17114 | Labs | LAB | LAB325 | unknown | PTT |
| -143 | Orders | DIET | DIET40 | unknown | DIET NPO |
| -143 | Orders | IVT | IVT3 | unknown | INSERT PERIPHERAL IV |
| -143 | Orders | NUR | NUR542 | unknown | VERIFY INFORMED CONSENT |
| -143 | Orders | COD | COD2 | unknown | FULL CODE |
| -143 | Orders | NUR | NUR2007 | unknown | VITAL SIGNS PER PROTOCOL |
| -143 | Orders | NUR | NUR105 | unknown | NURSING COMMUNICATION |
| -143 | Orders | NUR | NUR1016 | unknown | PREP SURGICAL SITE |
| -143 | Orders | ADT | ADT1 | unknown | ADMIT TO INPATIENT |
| -143 | Labs | LAB | LAB2776 | unknown | BLOOD BANK DRAW ONLY |
| -111 | Meds | ELECT/CALORIC/H2O | LACTATED RINGERS IV | unknown | LACTATED RINGERS IV |
| -111 | Meds | ANTIARTHRITICS | CELECOXIB 200 MG CAP | unknown | CELECOXIB 200 MG CAPSULE |
| -111 | Meds | ANALGESICS | OXYCODONE ER 10 MG | unknown | OXYCODONE CR (OXYCONTIN) tablet 20 mg |
| -111 | Meds | CNS DRUGS | PREGABALIN 75 MG CAP | unknown | PREGABALIN 75 MG CAPSULE |
| -92 | Meds | ELECT/CALORIC/H2O | LACTATED RINGERS IV | unknown | LACTATED RINGERS IV |
| -82 | Meds | ANESTHETICS | MIDAZOLAM 1 MG/ML | unknown | MIDAZOLAM 1 MG/ML INJECTION |
| -41 | Orders | ADT | ADT7 | unknown | TRANSFER PATIENT |
| -34 | Labs | LAB | LAB3038 | unknown | URINALYSIS WITH REFLEX CULTURE |
| -27 | Meds | ANTIBIOTICS | CEFAZOLIN 2000 MG INF | unknown | CEFAZOLIN 2000 MG INFUSION 50 |
| -14 | Labs | LAB | LAB359 | unknown | URINE CULTURE |
| -14 | Labs | LAB | LAB347 | unknown | URINALYSIS |
| 32 | Orders | NUR | NUR2007 | unknown | VITAL SIGNS PER PROTOCOL |
| 32 | Orders | NUR | NUR502 | unknown | EDUCATION, SMOKING CESSATION AND SECO |

FIG. 9

CONSENSUS SEQUENCE IDENTIFICATION

CROSS REFERENCE TO RELATED APPLICATIONS

This application is a continuation of U.S. patent application Ser. No. 14/597,156, filed Jan. 14, 2015, entitled "Consensus Sequence Identification," which claims the benefit of U.S. Patent Application Ser. No. 61/964,800, filed Jan. 14, 2014, entitled "System and Method for Stratifying and Predicting Consensus Patterns and Outcomes in Hierarchical and Temporally Ordered Events," which are hereby incorporated by reference herein.

TECHNICAL FIELD

The present disclosure generally relates to determining a consensus sequence from historical information and, more particularly, to techniques for copying content from applications when the applications are configured to different application states identifying consensus temporal patterns from past records of sequences of actions according to some quality metric(s) of interest.

BACKGROUND

As computers grow in both storage capacity and processing power, the collection of data has exploded. Unfortunately, as the amount and complexity of stored data grows, the ability to derive meaningful information from the stored data has been limited.

Data scientists have traditionally collected previously stored data and attempted to derive meaningful information through a query-based approach whereby a corpus of data is queried. Unfortunately, query-based approaches requires data scientists to guess at relationships in the stored data and then craft a meaningful query. Such an approach has limited value particularly as the amount and complexity of the data expands. Further, mistakes in formation of the query may lead to misleading results.

SUMMARY

An example method comprises receiving historical information of episodes, constructing event sets from the historical information, categorizing each event with general labels and synthetic labels, learning an event metric on the events by using the general and synthetic labels to perform dimensionality reduction to associate a vector with each event and to determine an angle between every two vectors, determining an event set metric using distances between each pair of event sets, deriving a sequence metric on the episodes, the sequence metric obtaining a preferred match between two episodes, deriving a subsequence metric on the episodes, the subsequence metric is a function of the event set metric on subsequences of each episode, grouping episodes into subgroups based on distances, for at least one subgroup, generating a consensus sequence by finding a preferred sequence of events, and the episodes of the subgroup, and generating a report indicating the consensus sequence.

Categorizing each event with general event category labels may comprise retrieving an ontology in the historical information and using the ontology to determine the general event category labels. In some embodiments, the preferred match between two episodes is an optimal match. The sequence metric may be a CP metric. The subsequence metric may be an ESCP metric.

In various embodiments, the function of the event set metric is a weighted sum. Each subsequence may be defined relative to one or more anchor points in the related episode. In some embodiments, each event includes a plurality of events. An order of the plurality of actions of at least one of the events is not distinguishable. Constructing event sets from the historical information may comprise constructing sets of events separated by no more than a predetermined period of time. The method may further comprise filtering the events to remove events that happen infrequently.

An example system may comprise an event set construction module, a categorization module, a categorization module, a metric construction module, a distance module, an episode metric assembly module, an autogroup module, and a consensus module. The event set construction module may be configured to receive historical information of episodes, each episode including at least one sequence of events taken over a period of time, and to construct event sets from the historical information, each of the event sets including at least one sequence of events. The categorization module may be configured to categorize each event from the historical information with general event category labels and synthetic event category labels. The metric construction module may be configured to learn an event metric on the events by using the general event category labels and synthetic event category labels to perform dimensionality reduction to associate a vector with each event and to determine an angle between every two vectors. The distance module may be configured to determine an event set metric using distances between each pair of event sets using the event metric. The episode metric assembly module may be configured to derive a sequence metric on the episodes to compute distances between episodes, the sequence metric obtaining a preferred match between two episodes with respect to a cost function describing a weighting for the event set metric, and to deriving a subsequence metric on the episodes to compute distances between episodes, the subsequence metric is a function of the event set metric on subsequences of each episode. The autogroup module may be configured to group episodes into subgroups based on distances obtained using the sequence metric and the subsequence metric. The consensus module configured to, for at least one subgroup, generate a consensus sequence by finding a preferred sequence of events with respect to a function of the sequence metric and the subsequence metric between the preferred sequence and the episodes of the subgroup and to generate a report indicating the consensus sequence.

An example computer readable medium may comprise executable instructions. The executable instructions being executable by a processor to perform a method. The method may comprise receiving historical information of episodes, constructing event sets from the historical information, categorizing each event with general labels and synthetic labels, learning an event metric on the events by using the general and synthetic labels to perform dimensionality reduction to associate a vector with each event and to determine an angle between every two vectors, determining an event set metric using distances between each pair of event sets, deriving a sequence metric on the episodes, the sequence metric obtaining a preferred match between two episodes, deriving a subsequence metric on the episodes, the subsequence metric is a function of the event set metric on subsequences of each episode, grouping episodes into subgroups based on distances, for at least one subgroup, generating a consensus sequence by finding a preferred sequence of events, and the episodes of the subgroup, and generating a report indicating the consensus sequence.

BRIEF DESCRIPTION OF THE DRAWINGS

FIG. 8a is an example illustration of neighborhood graph with clusters in some embodiments.

FIG. 8b is an example illustration of aligned event sets in a cluster core in some embodiments.

FIG. 8c is an example illustration of a consensus episode for cluster core in some embodiments.

FIG. 9 is an example event set with one anchor point event showing numbered groups in some embodiments.

Like reference symbols in the various drawings indicate like elements.

DETAILED DESCRIPTION

Example techniques to identify beneficial consensus temporal patterns from past records of sequences of actions is described herein. By selecting sets of past sequences of actions that were generally successful according to some quality metric(s) of interest, the consensus sequence produced may form a template for beneficial future actions.

In various embodiments, a sequence of actions taken over a finite period of time (an "episode") comprises sequences of sets of one or more "events." An event includes complex actions of some son including, but not limited to, giving a patient medication, drilling an oil well, or issuing an order to buy stock. By establishing a measure of similarity between episodes, we can partition them into clusters and derive a consensus (e.g., an average) sequence of events for each cluster, which will form a consensus sequence.

Various embodiments include construction of an appropriate sequences of event sets, one or more metric(s) on events, one or more metric(s) on event sets, and one or more metric(s) on episodes. A procedure may subsequently be formulated for deriving consensus sequences from clusters of episodes. Example systems and methods are also described herein for predicting an outcome of episodes that were previously not observed.

Although systems and methods described herein demonstrate an application in health care (e.g., constructing carepaths that are sequences of interactions between care providers and patients) and a reduction to practice in the same domain, it will be appreciated that the same and/or similar techniques may be applied to any number of fields (e.g., oil and gas, finance, biotechnology, and/or the like).

Figure 1:
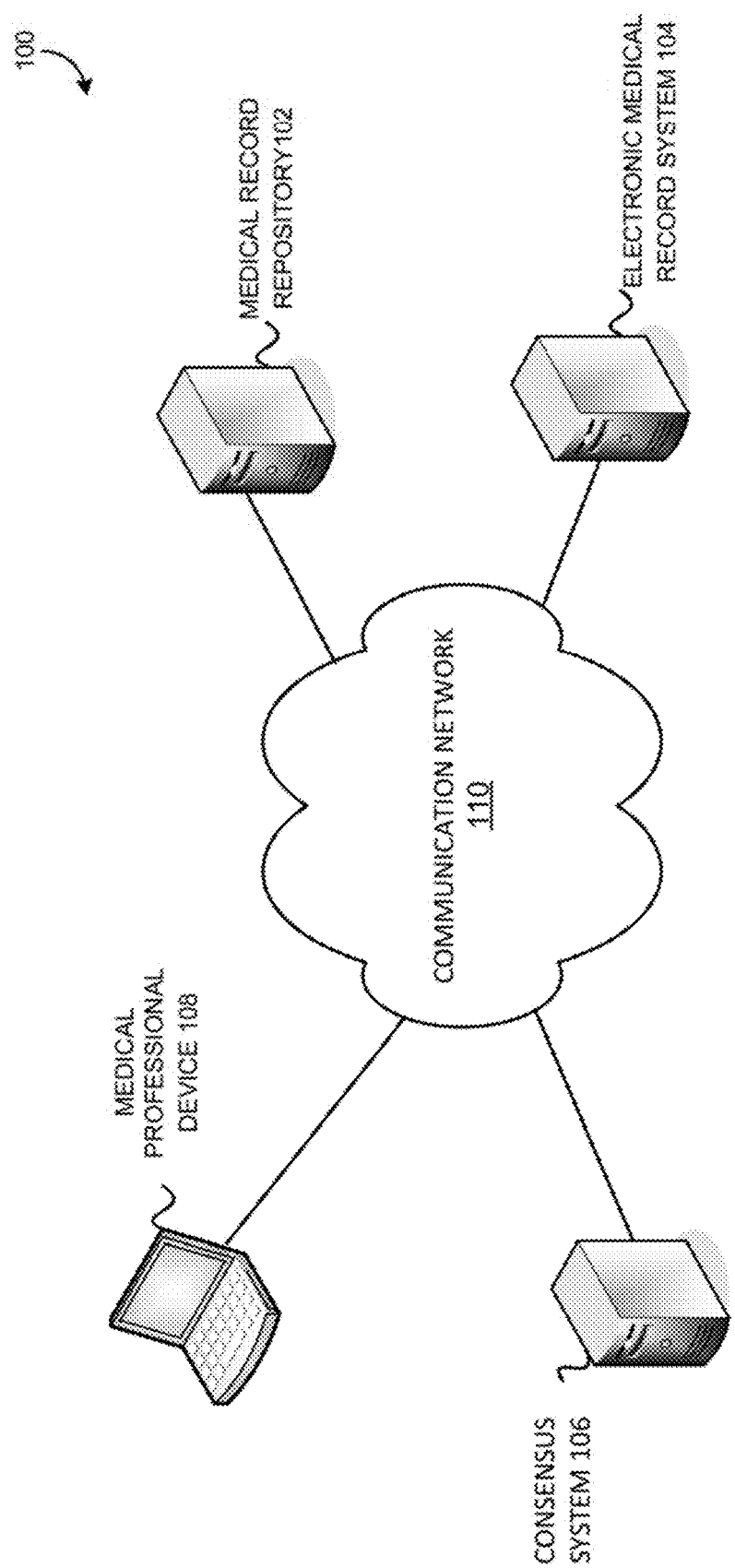
FIG. 1 is an example environment in which embodiments may be practiced.

FIG. 1 is an example environment 100 in which embodiments may be practiced. In various embodiments, data analysis for consensus sequence generation and/or outcome prediction may be performed locally (e.g., with software and/or hardware on a local digital device), across a network (e.g., via cloud computing), or a combination of both. There are many advantages between performing all or some activities locally and many advantages of performing all or some activities over a network. Although FIG. 1 is described regarding medical systems and devices, as discussed herein, it will be appreciated that there embodiments described herein may be used in any number of fields.

Environment 100 comprises a medical record repository 102, electronic medical record system 104, a consensus system 106, and a medical professional device 108 in communication over a communication network 110. Environment 100 depicts an embodiment wherein functions are performed across the communication network 110. In this example, a physician or patient may take advantage of cloud computing by storing data in a data storage server over a communication network 110. The consensus system 106 may perform analysis and generation of an consensus sequence report and/or prediction based on consensus sequences.

The medical record repository 102, electronic medical record system 104, consensus system 106, and medical professional device 108 may be or include any number of digital devices. A digital device is any device that comprises memory and a processor. Digital devices are further described in FIG. 18. A system may be any number of digital devices.

In various embodiments, the medical record repository 102 may include any amount of historical information (e.g., historical patient data). The medical record repository 102 may include, for example, an Electronic Medical Record (EMR) database. In one example, the medical record repository 102 may collect information from any number of medical professionals and related professionals (e.g., information from insurance companies) regarding any number of patients. For example, the medical record repository 102 may include medical records indicating treatment, labs, testing, operations, medicines, and/or the like related to any number of patients.

In various embodiments, the medical record repository 102 may include any amount of information regarding patients at multiple medical facilities and/or associated with any number of medical personnel. In some embodiments, the historical data of the medical record repository 102 may include historical information regarding any number of patients.

The electronic medical record system 104 may include any number of patient records (e.g., patient data) for any number of patients. In one example, the electronic medical record system 104 may receive and provide medical information regarding any number of patients for any number of physicians. In one example, the electronic medical record system 104 may include local patient information (e.g., patient information for any number of patients of a hospital or the like) and/or current information (e.g., labs to be performed and/or the like).

The medical professional device 108 is any device associated with a medical professional. In various embodiments, a physician may utilize the medical professional device 108. In various embodiments, the medical professional device 108 may provide patient information to the medical record repository 102 and/or the electronic medical record system 104. The medical professional device 108 may receive consensus sequence report (e.g., carepaths) based on patient historical data and/or provide predictions based on the consensus sequences discovered and current patient information. The medical professional and/or the medical professional device 108 may assess the consensus sequence report in view of a patient to determine a preferred course of action.

The communication network 110 may be any network that allows digital devices to communicate. The communication network 110 may be the Internet and/or include LAN and WANs. The communication network 110 may support wireless and/or wired communication.

The consensus system 106 is a digital device that may be configured to analyze data (e.g., historical patient information from the electronic medical record system 104) to generate the consensus sequence report (e.g., a report indicating a consensus temporal patterns from past records of sequences of actions performed).

The consensus system 106 may also receive patient information from the medical professional device 108 and provide a course of action or assessment based on the received patient information and the consensus sequences discovered. An example consensus system 106 is described with regard to FIG. 2.

Figure 2:
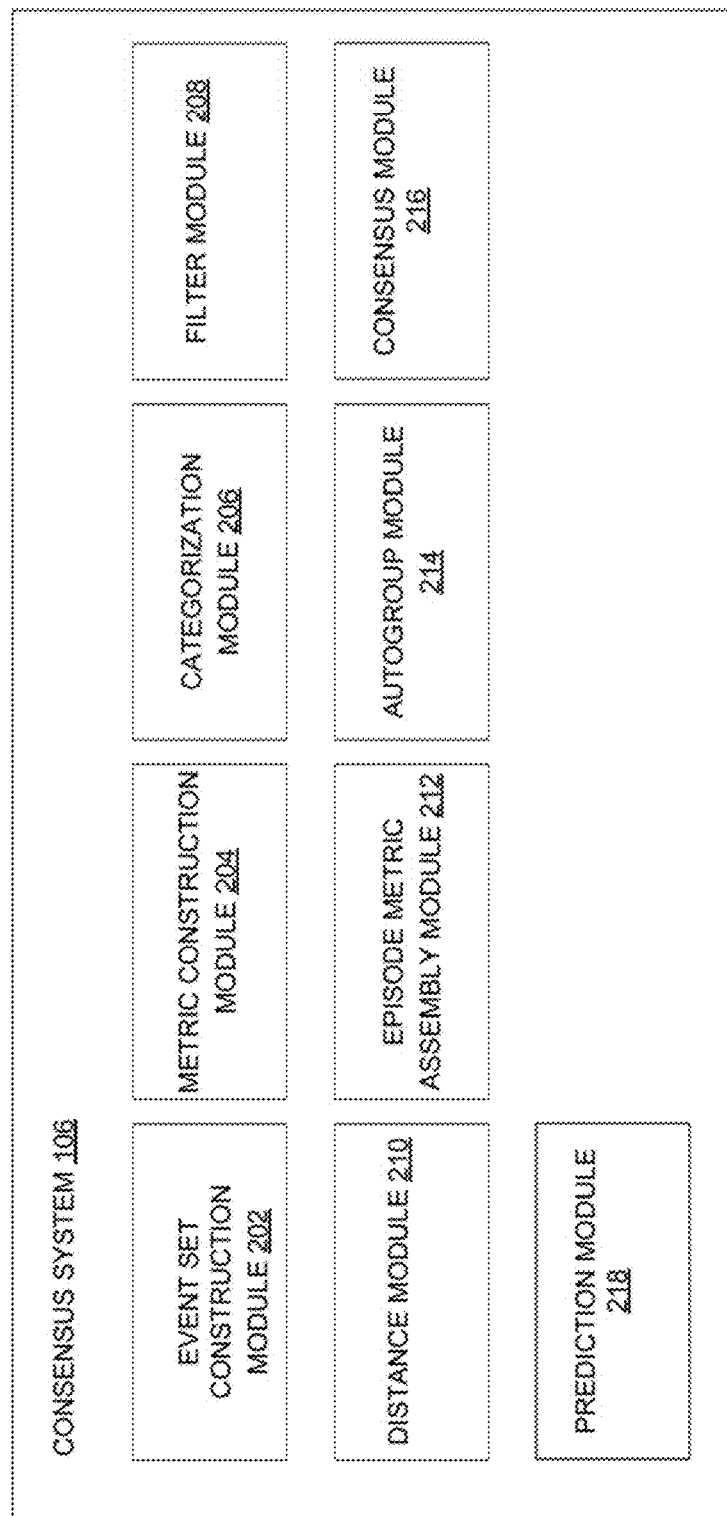
FIG. 2 is a block diagram of an example consensus system in some embodiments.

FIG. 2 is a block diagram of an example consensus system 106 in some embodiments. The consensus system 106 may comprise an event set construction module 202, a metric construction module 204, a categorization module 206, a filter module 208, a distance module 210, an episode metric assembly module 212, an autogroup module 214, a consensus module 216, and a prediction module 218. Each module is described herein with a more detailed example discussed with regard to the flowchart of FIG. 3.

In various embodiments, the event set construction module 202 is configured to construct event sets and episodes from events. Events in an event set are actions (e.g., interactions) whose order may be indistinguishable (e.g., a collection of tests ordered by a doctor at one time). An episode is then a sequence of these event sets.

For example, the event set construction module 202 may receive data from any number of sources, such as, for example, a medical record repository 102 and/or an electronic medical record system 104. The data may, for example, include medical information regarding any number of patients. The data may include, in some embodiments, a patient identifier and any amount of information for that patient including for example, medical tests, when medical tests were assigned, medical procedures (e.g., X-rays, surgeries, or the like, application of medicines), when the medical procedures were assigned and/or performed, outcome assessment, prognosis, symptomology, and/or the like.

Data may come from any number of databases. A database may be any data structure containing data (e.g., a very large dataset of multidimensional data). In some embodiments, the database may be a relational database. In some examples, the relational database may be used with MySQL, Oracle, Microsoft SQL Server, Aster nCluster, Teradata, and/or Vertica. Those skilled in the art will appreciate that the database may not be a relational database.

In some embodiments, a user identifies a data structure and then identifies ID and data fields. Data S may be based on the information within the ID and data fields. Those skilled in the art will appreciate that data S may be a finite metric space, or a generalization thereof, such as a graph or weighted graph. In some embodiments, data S may be specified by a formula, an algorithm, or by a distance matrix which specifies explicitly every pairwise distance.

In various embodiments, a metric is constructed on episodes which allows a quantitative attribution of a degree of difference (or equivalently, similarity) between at least two episodes by (e.g., optimally) pairing event sets, and then using a metric on a plurality (e.g., a pair) event sets. In some embodiments, a carepath metric (CP) (e.g., a sequence metric) uses both of these steps, and an event set carepath metric (ESCP) (e.g., a subsequence metric) utilizes only the latter step. The construction of both these metrics is will be described at length below.

In what follows, we show how to construct appropriate sequences of event sets, a metric on events, a metric on event sets, and finally a metric on episodes. We then formulate a procedure for deriving consensus sequences from clusters of episodes. We also describe a method for predicting the outcome of episodes that were previously not observed. Finally, we demonstrate an application in health care (constructing carepaths, i.e. sequences of interactions between care providers and patients) and a reduction to practice in the same domain.

The metric construction module 204 is configured to learn a metric on the events from the data. In some embodiments, the metric construction module 204 constructs available episodes (e.g., sequences of event sets) from the received data as described herein. The metric construction module 204 may utilize the categorization module 206. The categorization module 206 may categorize events in the received data. In some embodiments, the categorization module 206 may receive tags or other categories from another source. For example, all or some of the events identified by the received data may be assigned categories (e.g., the all or some of the events in the received data may be associated with metadata that may be used to categorize the events). In one example, the categorization module 206 may receive an ontology that may be used to categorize events. In one example, various events performed in a hospital may be assigned a category (e.g., LABS). The received data may include, for example, descriptions of events and categories.

In various embodiments, the categorization module 206 may generate or receive categories (e.g., "general categories") of events. The categorization module 206 may, for example, generate categories based on metadata or other information associated with the received data. For example, the categorization module 206 may generate categories of events from the received data by using some of the data associated with the events to generate categories (e.g., based on natural language processing, semantic analysis, times of events relative to other events, available metadata describing the event, type of patient involved in the event, type of doctor or medical professional involved in the event, and/or the like).

The categorization module 206 may generate synthetic categories for events as well as general categories of events. A synthetic category may be, for example, a more generic or broader category that the general category (e.g., the synthetic category may be broader or more abstract than the categories provided as a part of the ontology). It will be appreciated that an event may be assigned two or more categories (e.g., a general and a synthetic category).

The filter module 208 may optionally filter (e.g., prune) events that occur too infrequently to be discriminated. In some embodiments, the filter module 208 utilizes one or more aggregation function(s) to identify and/or filter events (e.g., eliminate infrequent events). For example, the filter module 208 may aggregate frequencies of events across multiple patients to determine relative frequency for any number of events. Utilizing the aggregation, the filter module 208 may generate a frequency threshold (e.g., lowest 5%) to filter out events that fall below the generated frequency threshold.

In various embodiments, the filter module 208 identifies events that are to be filtered (e.g., removed) by utilizing the frequency threshold and subsequently replaces the events to be filtered with an instance of a synthetic category associated with the general category. In some embodiments, the filter module 208 replaces events to be filtered with an instance of a synthetic event (e.g., another event associated with the synthetic category). It will be appreciated that replacing events to be filtered with synthetic events or maintaining the event and changing the assigned category (e.g., to the synthetic category) may reduce noise.

Returning to the metric construction module 204, the metric construction module 204 may learn a metric on events using the categorization(s). The following discusses metric learning at a high level. A more detailed description may be found in the discussion regarding flow chart 3.

In various embodiments, the metric construction module 204 utilizes dimensionality reduction to make a metric on the events. A "context" may be defined from the event set. The context may be the collection of categories present on the set which may be vectorized by assigning a dimension to each category and further normalize to a norm value (e.g., a Euclidean norm value equal to one).

For each event, the metric construction module 204 may sum the contexts of all the event sets to which the event belongs. As a result, each event may be associated with a unit vector and the angle between such vectors may be used as the basis for a metric on the events.

The distance module 210 may compute a distance between event sets (e.g., using a greedy algorithm on the pairs of elements of each group). For example, the distance module 210 may determine the distances from all pairs of the two sets, removing exact matches.

The episode metric assembly module 212 may be configured to generate two metrics on episodes including, for example, a CarePath (CP) metric and an Event Set Care Path (EPSC) metric. Both rely on event "anchoring," the idea behind which is that the events and event sets in a pair of episodes have some intrinsic relationship due to their relative episodes, not just due to the precise events themselves. For example, there may be a difference between events which occur before surgery and those which occur after, and making this explicit may be significant. There is some sense in which this might be called an optimization (in the divide-and-conquer sense) but the improvement is not just in speed: using anchoring may also greatly reduce noise.

With one anchor point event, groups may be numbered with decreasing negative numbers before surgery and increasing positive numbers after surgery. With multiple anchor points, event-groups before the earliest anchor point may be numbered with decreasing negative values, and after each anchor point multi-indices (one for the anchor index and one for the event-group ordinal). Rules may be established (including penalties) for pairings between different anchor groups—for example, for surgical treatments an example rule is no pairing between pre- and post-surgical groups.

FIG. 9 is an example event set with one anchor point event showing numbered groups in some embodiments. Time 902 depicts events being numbered with decreasing negative numbers before surgery and increasing positive numbers after surgery. The parent category 904 may be a synthetic category and the category 906 may be a general category provided in the received data. The code 908 may be codes associated with events while the interval 910 may be a duration of the event. The description 912 may provide additional information regarding the event.

In various embodiments, the episode metric assembly module 212 may construct the CP metric using a modified version of dynamic time warping (DTW). DTW is a well known algorithm for measuring similarity between two temporal sequences which may vary in time or speed. The episode metric assembly module 212 may use DTW to match event groups in a pair of episodes to define a distance.

In computing the ESCP metric, the episode metric assembly module 212 may match (e.g., unconditionally) events by anchor value. This matching may identify subset(s) with substantial overlap in events to aid in the construction of a consensus.

The autogroup module 214 may autogroup subgroups using the CP metric. In various embodiments, data points of a data set or nodes in a graph are automatically grouped (i.e., "auto-grouped"). The groupings may be approximations of a possible maxima (e.g., a best maxima) of a given scoring function (e.g., the CP metric) that scores possible partitions of the original object (i.e., a collection of data points or a collection of nodes of a graph).

Auto-grouping may be utilized to automatically find a collection of subsets of some set Y that share one or more given properties. In one example, auto-grouping may be utilized to find a collection of subsets that is a partition of Y where Y is a subset of a finite metric space X or nodes in a graph. However, it will be appreciated, based on the disclosure, that the methodology described herein has no such requirement.

In various embodiments, a selection of possible partitions of a data set (e.g., original data set or nodes in a visualization) may be identified and scored. A partition is a collection of disjoint subsets of a given set. The union of the subsets of each partition equal the entire original set. A hierarchical clustering method may be utilized on the original object Y to create a family of partitions of Y.

Auto-grouping is the process in which this highest scoring partition is identified. The highest scoring partition may be the maximum of the given scoring function(s). In some embodiments, a limited number of partitions of possible partitions may be generated. In fact, in some cases, the result may be better if the scorer is imperfect, as at least some hierarchical clustering algorithms generally avoid partitions with large numbers of miscellaneous singletons or other ugly sets which might actually be the global extreme for such a scoring function. It will be appreciated that the hierarchical clustering process may serve to condition data to only present "good alternatives," and so can improve the effectiveness of some scorers.

Since the number of partitions for a data set is high (e.g., $(N/\log(N))^N$), it may be impractical to generate every possible partition. Unfortunately, most local improvement methods can easily get stuck. Some techniques to generate a subset of partitions involve attempting to maximize a modularity score over graph partitions by making an initial partition and then making local changes (e.g., moving nodes from one partition to another). Modularity is the fraction of edges that fall within given groups minus the expected such fraction if edges were distributed at random. Unfortunately, the modularity measure Q score typically exhibits extreme degeneracies because it admits an exponential number of distinct high-scoring solutions and typically lacks a clear global maximum. Another approach to maximizing functions on partitions by local methods is to use probabilistic techniques such as simulated annealing. At least some embodiments described herein offer a deterministic alternative that is applicable to a wide range of scoring functions.

Subsets in one or more different partitions of those generated may be selected based, at least in part, on the CP metric values. A new partition including the selected subsets may be generated or, if all of the selected subsets are already part of a generated partition, then the preexisting partition may be selected.

An example of autogrouping using scoring functions is discussed regarding FIGS. 14-17. It will be appreciated that autogrouping may be performed using any scoring function such as, for example, CP metric values.

The consensus module 216 may be configured to find a core of the autogrouped subsets (e.g., from the selected partition of the autogroup module 214). For example, given a subset of episodes S, the consensus module 216 may compute the points x in S such that the sum(y in S) CP(x,y) is smallest: we refer to such points as those of "maximum centrality" in S under CP. Given this most central subset using CP (call this M), the consensus module 216 then finds the most central subset of M using ESCP, and it is this subset the consensus module 216 denotes as the core C of S.

In various embodiments, having computed the core, the consensus construction is an optimization problem: we are looking for a candidate sequence of event-sets c such that Q(c, S)=sum(y in C) CP(c,y) is minimized, subject to a "believability" constraint: the events in c cannot be unrealistic. Specifically, in one example, this means that the consensus module 216 may start with an actual episode, and then edits it conservatively, keeping edits such that Q(c,S) improves. The consensus module 216 may use any optimization techniques (one level backtracking with a greedy algorithm).

The prediction module 218 is configured to predict outcomes of novel episodes (i.e., proposed courses of action) using the distance measures described herein. Using a linear combination of one or more such distance matrices, and values of dependent outcome variables, the prediction module 218 may construct a predictor that can predict the values of dependent outcome variables given input of new entity states, episodes, or a combination of both.

Modules, engines, and data stores included in the consensus system 106 and elsewhere in the description, represent features. The modules and data stores described herein may be embodied by electronic hardware (e.g., an ASIC), software, firmware, or any combination thereof. Depiction of different features as separate modules and data stores does not necessarily imply whether the modules and data stores are embodied by common or separate electronic hardware or software components. In some implementations, the features associated with the one or more modules and data stores depicted herein may be realized by common electronic hardware and software components. In some implementations, the features associated with the one or more modules and data stores depicted herein may be realized by separate electronic hardware and software components.

The modules and data stores may be embodied by electronic hardware and software components including, but not limited to, one or more processing units, one or more memory components, one or more input/output (I/O) components, and interconnect components. Interconnect components may be configured to provide communication between the one or more processing units, the one or more memory components, and the one or more I/O components. For example, the interconnect components may include one or more buses that are configured to transfer data between electronic components. The interconnect components may also include control circuits (e.g., a memory controller and/or an I/O controller) that are configured to control communication between electronic components.

Figure 3:
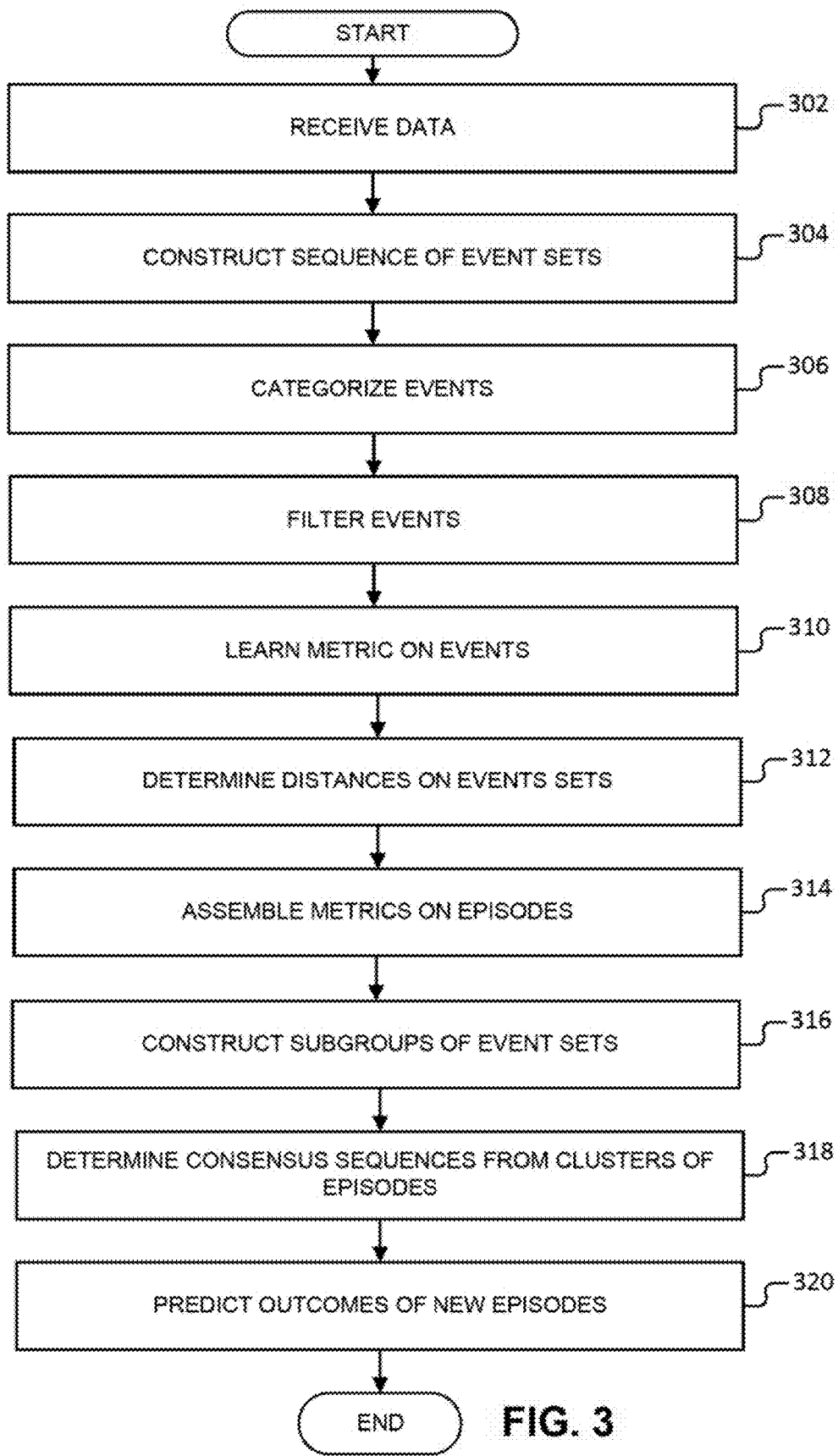
FIG. 3 is a flowchart of a method for generating consensus temporal patterns in some embodiments.

FIG. 3 is a flowchart of a method for generating consensus temporal patterns in some embodiments. In step 302, historical information is received. For example, the event set construction module 202 may receive historical information (e.g., historical medical information) regarding any number of patients.

In various embodiments, the event set construction module 202 is configured to construct event sets from the received data and episodes from events. The events in an event set are actions (e.g., interactions) whose order may be indistinguishable (e.g., a collection of tests ordered by a doctor at one time). An episode is then a sequence of these event sets.

In various embodiments, a metric is constructed on episodes to allow quantitative attribution of a degree of difference (or equivalently, similarity) between at least two episodes by (e.g., optimally) pairing their event sets, and then using a metric on pairs of event sets. In some embodiments, a carepath metric (CP) uses both of these steps, and a event set carepath metric (ESCP) utilizes only the latter step.

Figures 4, 5, 6:
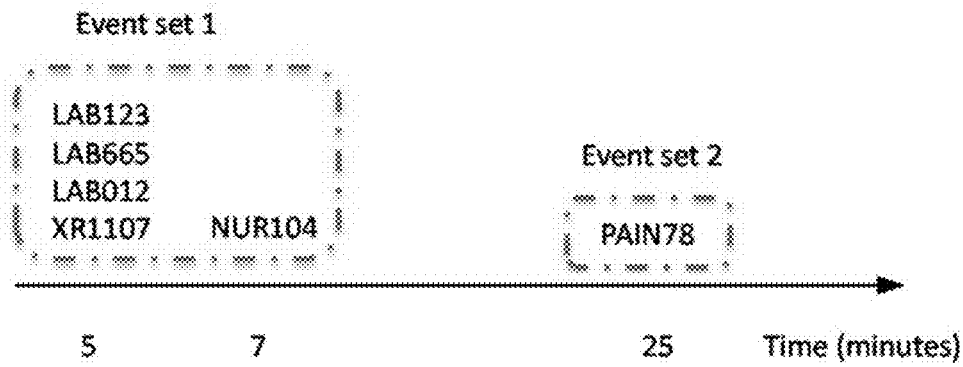
FIG. 4 is an example illustration of events in received data in some embodiments.
FIG. 5 is an example illustration of unit vectors in a Euclidean space of moderate dimensionality in some embodiments.
FIG. 6 is an example illustration of unmatched pairs are paired with generic events in some embodiments.

In step 304, the event set construction module 202 constructs sequences of event sets. To construct the event sets, the event set construction module 202 may utilize one or more heuristic(s) that specifies which events belong to a set. Here, sets may be constructed that are separated by small amounts of time (See FIG. 4). It will be appreciated that any amount of time may be used (e.g., ranging from 30 seconds up to 2 hours). In some testing, we found that the resulting metric on events was the least noisy at 5 minutes. Given that the time scales of actions for other problems are quite different, we are fairly certain this number would need to be revised for such occasions.

The metric construction module 204 may be configured to learn a metric on the events from the data. In some embodiments, the metric construction module 204 constructs all or some of the available episodes (e.g., sequences of event sets) from the received data. The metric construction module 204 may require categorization and/or filtering on the events.

In step 306, the categorization module 206 assigns events categories. For example, the categorization module 206 may assign events to higher-level groups (e.g., categories) by a supplied ontology. For example, various lab tests in a hospital may belong to the category LABS. These categories are utilized in the metric construction example described herein.

In some embodiments, the categorization module 206 creates a synthetic event category for any number of categories (e.g., for any number of categories provided by the supplied ontology). As discussed herein, a synthetic category may be, for example, a more generic or broader category that the general category (e.g., the synthetic category may be broader or more abstract than the categories provided as a part of the ontology). It will be appreciated that an event may be assigned two or more categories (e.g., a general and a synthetic category).

For example, the synthetic event category for LABS may be labeled "GENERIC LAB," and be understood to be a placeholder for some as yet unknown lab. Note that the category of a generic event may be defined to be a category for which that generic event was created.

In some embodiments, the metrics on the event-groups depend on having a metric on the events. If a metric on the event-groups is not given, the metric construction module 204 may construct a metric on the event-groups using the data. As discussed herein, events may be grouped in categories. The categories may be used to construct a metric on the events.

In step 308, the filter module 208 optionally filters events which occur too infrequently to be discriminated. In some embodiments, the filter module 208 utilizes one or more aggregation function(s) and to identify and/or filter (e.g., eliminate infrequent events). In one example, the filter module 208 generates a cumulative distribution using a cumulative distribution function for event frequencies and filter (e.g., "throw out") the 5% tail. In some embodiments, the filter module labels events 0 for the most common event, 1 for the next most common, and so on. The filter module 208 may then filter or (e.g., remove or eliminate) every event beginning with the number such that the total count of events from that number on is <=5% of the total number of events. In various embodiments, the filter module 208 utilizes a filter process that replaces the event with an instance of the synthetic event for that same category. It will be appreciated that this step may noticeably reduce noise in the resulting event metric space.

In step 310, the metric construction module 204 learns a metric on events using the categories and/or filtered events. In various embodiments, there may be an order of magnitude more types of events than categories (i.e., the dimensionality of the category space is much lower than that of the event space). We use this dimensionality reduction to make a metric on events. We define a "context" from an event set to be the collection of categories present in that set. For example, if a surgeon orders three lab tests and chest-x-ray at one time, this forms a set which looks like:

---
{"COMPREHENSIVE METABOLIC PANEL,"
"CBC WITH DIFFERENTIAL,"
"LIPASE, "
"XR CHEST PA AND LATERAL"}
---

What this does is generate a "context" {LAB, LAB, LAB, XRAY}. The metric construction module 204 may vectorize these contexts by assigning each category a "dimension" in a Euclidean Space. If we suppose that XRAY is given dimension 2 and LAB dimension 4, then the vectorized context above would look like {0, 0, 1, 0, 3, ... } where all the other entries are 0. We further normalize these contexts so that they have Euclidean norm=1, which means the context becomes {0, 0, 1/sqrt(10), 0, 3/sqrt(10), ... }.

Now for each event, the metric construction module 204 may take the sum of the contexts of all the event sets to which that event belongs, and for synthetic events the metric construction module 204 may sum all the contexts for any event which has the same category as the synthetic event. After vector normalization, this may give every event (including synthetics) a unit vector in a Euclidean space of moderate dimensionality, and the angle between such vectors is used as the basis for a metric on the events (See FIG. 5 for example).

It will be appreciated that there may be a large number of event sets which are singletons. This lack of "additional information" (i.e., no context) means that the metric may not resolve these actions effectively. In various embodiments, the operation may be changed to add a value (e.g., 0.01) times the context before and/or after the event-set containing an event (including synthetics), assuming such event-sets exist. This small change may have the desired result without perturbing the rest of the metric. And second, because synthetic events were by their very definition indefinite, distance between a generic event and any other event may be defined in terms of the "dispersion" for real events of that category.

The dispersion of a category may be defined in any number of ways. For example, dispersion of a category may be defined to be square-root of the average of the squares of the angle distance between the synthetic vectorization and all the vectorizations of real events. This gives a measure of how "smeared out" the vectorizations for events in a category are, and may be a reasonable measure of the distance between a synthetic and non-synthetic event. For a pair of synthetic events, the distance is the dispersion if they have the same category, else it is the sum of their individual dispersions plus the angle distance between their respective vectorizations. The dispersion for any real event may be defined to be 0.

As an optimization, since there are not a very large number of distinct events, the metric construction module 204 may pre-compute and cache the distance matrix for the event space.

If events are not equipped a priori with an ontology that produces a categorization on the events, the categorization may be inferred from the data using a simple iterative algorithm. For example, the categorization module 206 may produce the full N×N co-occurrence matrix for all events, and use standard clustering algorithms to define clusters in that space (producing M<N clusters). The metric construction module 204 may take those clusters to be the categories described above, and re-learn the event metric in M-dimensional space. The metric construction module 204 may cluster again in this space, producing M'<M clusters, and re-learn the event metric in M'-dimensional space. The metric construction module 204 may iterate until the procedure converges and take the final clustering as the correct categorization.

In step 312, the distance module 210 computes a distance between event sets G1 and G2. In one example, the distance module 210 computes a distance between event sets G1 and G2 by using a greedy algorithm on the pairs of elements from each group. For example, the distance module 210 may remove exact matches (adding their distances—which will be 0 unless some synthetic events are present), and then the distance module 210 may compute the distances for all (remaining) pairs in the two sets. The distance module 210 may remove pairs greedily (shortest distances first, if both events are still in their respective sets), and then any left-over unmatched pairs are paired with generic events (See FIG. 6). It will be appreciated that this may be a straightforward extension of the typical solution to the pairing problem in dynamic time warping (which may be utilized herein) where a single type of "no match" event exists. However, it will be appreciated that there are any number of other pairings (e.g., using the Hungarian algorithm) which the distance module 210 might apply.

When pairing events A and B two different event-groups, the distance module 210 may consider two cases: the event distance between A and B, and the sum of the distances between A the synthetic version of A and B and the synthetic version of B. The distance module 210 may take the smaller of these two values as the pairing distance for A and B. As part of this process the distance module 210 may sometimes save the explicit match between event groups. In one example, the distance module 210 may incorporate this code in the distance computation under the control of a Boolean flag.

To be more specific, in some embodiments, if we let eva stand for the array of event objects sorted by integer event codes for the "A group" and evb for the "B group" we can use a zipper algorithm to copy the arrays of events into temporary integer stacks sa and sb containing the indices into eva and evb respectively (excepting any exact matches). We increment the return value by the distance between these exact matches, which are zero unless the matching events are generic. If we are preserving the explicit match, we save the pairs which matched exactly at this point in a separate stack of event pairs.

We then store all pairs of unmatched events as float/int/int triples f/i/j as a packed 64-bit Java long integer: here the float is the minimum of the event distance between the events eva[sa(i)], evb[sb(j)] and the sum of the event distances between the events eva[sa(i)] and evb[sb(j)] and their generics. We can use regular 'long sorting' in Java to sort these triples as f is in IEEE 32-bit format and >=0.0f.

We iterate over the sorted triples removing any pair we encounter when both elements are still present (clearing the respective entries in sa/sb so we know they were removed), and incrementing the return value by f. When we have emptied one of sa/sb, we stop and process any remaining sb/sa entries, incrementing the return value by the distance between that entry and its generic. If we are saving the pairs for the exact match we also use the indices to extract the event pair from eva and evb. We then return the cumulative matching value.

In step 314, the episode metric assembly module 212 assembles metrics on episodes. As discussed herein, we introduced two metrics on episodes: the Care Path (CP) metric and the ESCP (Event Set Care Path) metric.

In some embodiments, to construct the CP metric, the episode metric assembly module 212 may use a modified version of dynamic time warping (DTIW, also known as sequence alignment) to match event-groups in a pair of episodes to define a distance. Here, an event set is a sequence of events (possibly including synthetic events) and a "synthetic" set is an event set composed entirely of synthetic events. If A is an event set, we define synth(A) to be the set formed by replacing every code in A by its generic form: for A={NUR1, CT5, GENERIC_XR}, then synth(A) is (GENERIC_NUR, GENERIC_CT, GENERIC_XR).

Suppose we have a metric d(A,b)>=0 defined on pairs of event sets which also has the property that d(A,*), for * synthetic, is minimized by d(A,synth(A)). Then we can define a metric on pairs of sequences of events even if the sequences are of different lengths. Given two sequences of sets AB . . . and ab . . . of the same length, we can define a "base metric" bd(AB . . . ,ab . . . ) as d(A,a)+d(B,b)+ . . . . We then extend this to two sequences of possibly different lengths ABC . . . and abc . . . by "editing" the sequences with insertions of "synthetic sets" to get pairs of sequences of the same length, and then taking the minimum value. If we denote any synthetic set by *, then we can define a distance between AB and abc as the min {bd(AB*,abc), bd(A*B*, a*bc), . . . }, over all possible equal length pairs of edits. This is well-defined because any possible pair of edits which have corresponding *'s can be edited to remove those matching synthetic sets (the value of sum of bd( )'s will not increase), and we know that every * can be replaced by the matching synth( ) event in the other sequence. From this we see that we are taking the minimum over a finite set of edits, and these edits can be thought of as pairs sequences of "pairings" of the form A<->x, Y<->*, or *<->z, which we call "diagonal," "horizontal," respectively "vertical" pairings, for reasons that will shortly become clear.

Figures 7A, 7B:
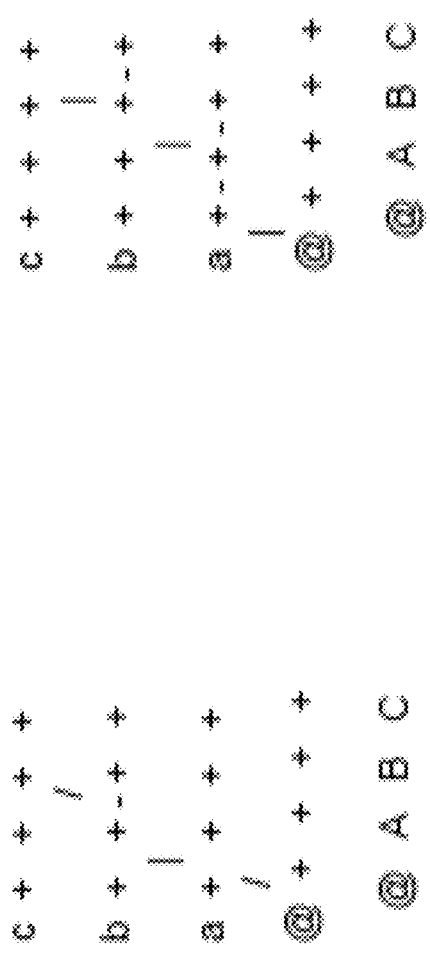
FIGS. 7a and 7b are example illustrations of pairings and paths in a grid in some embodiments.

Let @ be a special code that is otherwise unused. There is a natural correspondence between such pairings and paths (going to the right and up) in the grid with nodes labeled by pairs (x,y) where x ranges over {@,A,B,C, . . . } and y ranges over {@,a,b, . . . }. Going, up diagonally corresponds to diagonal pairing, while a vertical edge is a vertical pairing and a horizontal edge is a horizontal pairing. As examples, the matching ABC with abc of A*BC<->ab*c is shown in FIG. 7a; matching ABC with abc by AB*C*<->a**b*c is show in FIG. 7b.

Intuitively a path has a "component in the direction of a sequence element being consumed." The paths must begin in the lower left and go up and/or to the right to the upper right corner. Additionally, since we are looking for consensus on episodes, we probably can count on not being interested in paths with "sufficiently many" synthetic sets, so if the sequences are too different in length or too far from the diagonal, we probably can return a "large value" and quit. This suggests matching at the set level might be linear in the number of sets—and at least less than quadratic—as interesting paths would be constrained to be around the diagonal. To find the cost of the optimal path we only need a matrix of the same size as the grid in which all the paths lie. We assign to every grid point the minimum path cost to get to that point.

We can only get to a point (C,b) from (B,a), (C,a), or (B,b)), and there is only one way from each of these points to (C,b), so knowing those 3 values means we can compute the fourth—a perfect situation for dynamic programming (Note, in fact, that we only need the values for the current column and the previous one, which cuts down on the intermediate state required although not on the number of computations). We will denote this minimal cost state by the table MinCost(,)—that is a properly initialized MinCost(M, n) will be cost of the best pairing of the elements A, . . . , M with a, . . . , n, where MinCost(@,b) means pair *,* with a,b, (i.e. bd((*,*),(a,b)), and so forth. Naturally MinCost(@,@) is 0. Let us now denote the events A,B,C, . . . by g[0],g[1], etc. and a,b,c, . . . by the elements of the array h[ ]. Instead of MinCost( ) we will use a matrix DTW[i][j] defined to be MinCost(g[i−1],h[j−1])—that is, DTW[i][j] is the cost of the best path aligning the first i entries of g with the first j entries of h. (This reserves the index 0 for @.) DTW is M×N where M=g·length+1 and N=h·length+1, and the cost of the best path is DTW[g·length,h·length]. In pseudocode the matching is performed as per DIST( ) below, where synth(set) is the synthetic version of an event set and d(group,otherSet) is the non-negative symmetric distance between event sets:

```
DIST(g: sets [0..N−1], h: sets [0..M−1]) {
// DTW[x][y] is the cost of the minimal PATH which 'consumes' the first
// x elements of g and the first y elements of h - that is, the cost of
// the best path from (0,0) to (x,y) in the plane.
DTW := double[N+1][M+1]
```

-continued

```
// Fill in the values for the bottom row of the grid
for i := 0 to N-1
    DTW[i+1][0] := d(g[i],synth(g[i])) + DTW[i][0]) // horizontal
// Fill in the values for the left column of the grid
for j := 0 to M-1
    DTW[0][j] := d(synth(h[j]), h[j]) + DTW[0][j]) // vertical
for i := 0 to N-1
    for j := 0 to M-1
        DTW[i+1][j+1] :=
            min(d(g[i], h[j]) + DTW[i][j],        // diagonal
                d(g[i], synth(g[i])) + DTW[i][j+1], // horizontal
                d(synth(h[j]), h[j]) + DTW[i+1][j]) // vertical
return DTW[N, M]
}
DTW[0][j+1] = d(synth(h[j]), h[j]) + DTW[0][j] for all j>=0, because the
only possible path to (0,j) has the first j+1 entries matched with
synthetics. Similarly for DTW[i][0].
/
```

The event group distance may works as shown in pseudocode below. The idea is to penalize matchings of event sets whose indices are too far off from one another, so pairs of episodes may be rejected that are "too different."

```
public double eventSetDistance(Episode pA, EventSet a,
                Episode pB, EventSet b) {
    // Bail if the anchorCode's don't match - we can use this to avoid
    // splitting the anchor segments and doing DTW individually on them,
    // but the complexity of that is outweighed by the performance gain
    of
    // making the 'sides of the grid' smaller.
    if (a.anchorCode != b.anchorCode)
        return HUGE;
    // We take 2/3's of the 'average synthetic error' as the scale to make
    // the error 'slightly weaker' than the average synthetic
    // error.
    double sdError = (a.distanceToSynthetic +
    b.distanceToSynthetic)/3.0;
    double indexError = (a.zbIndex - b.zbIndex)/2.0;
    double incr = sdError * indexError * indexError;
    // The error is always included since even an exact match between
    // groups of widely different 'times' is still undesirable.
    return eventSetPairing(pA, a.events, pB, b.events, null) + incr;
}
```

The method eventSetPairing( ) does an unconditional matching of the pairs of events in the respective anchor sets from Episodes A and B and returns the resulting distance.

Finally, in computing the ESCP metric (used in the for the second step of consensus core computation below), the episode metric assembly module 212 may perform only the unconditional matching of events by anchor value (e.g., for surgical episodes we make positive and negative groups out of the events in each episodes and pair them and return the total error). In some embodiments, the set of episodes may have been reduced once to those which match up well as "time series" of event sets. This step tries to find a subset with substantial overlap in the actual events, to aid in the construction of a consensus.

The consensus module 216 may determine consensus sequences from clusters of episodes. Having learned the CP and ESCP metrics from the data, we now describe a clustering/portioning of episodes in the data source and a process for computing a consensus sequence from the partitions.

In step 316, subgroups of events sets are constructed. In various embodiments, the autogroup module 214 automatically constructs coherent subgroups using the carepath metric CP. In one example, the autogroup module 214 constructs a graph of the metric space using the 5 nearest neighbors for each point where the additive edge strength between points p and q is 1/(ordinalDistance(p,q)), where the ordinalDistance(p,q) is j if q is the jth nearest neighbor of p. Having constructed the graph, the autogroup module 214 autogroups using 95% as the "clustering cutoff." The autogroup module 214 then generates a partition of the nodes in the graph, and as those nodes are episodes, this partition gives rise to a collection of "related subsets" on which to search for a consensus (See FIGS. 8a-8b). It will be appreciated that any number of nearest neighbors may be utilized (e.g., not only five) and that the clustering cutoff may be any threshold (e.g., any percentage, discrete value, or the like).

As discussed herein, the process of autogrouping is described with regards to FIGS. 14-17.

Having reduced the problem to searching for a consensus carepath on a given subset, the consensus module 216 may find the "core" of the subset, and then the consensus module 216 processes the core to produce a consensus in step 318. Given a subset of episodes S, the consensus module 216 computes the points x in S such that the sum(y in S) CP(x,y) is smallest: we refer to such points as those of "maximum centrality" in S under CP. Given this most central subset using CP (call this M), the consensus module 216 then finds the most central subset of M using ESCP, and it is this subset the consensus module 216 denotes as the core C of S. We reject any input subset of length less than 40, since 20 is the minimum core size we have found usable, and we prefer sets with at least 100 points. To increase the probability that that these size constraints are satisfied, in the first step the consensus module 216 finds an M whose size is the minimum of 150 and (1/sqrt(2.0)) times the size of S. The size of C is taken to be the minimum of 100 and (1/sqrt(2.0)) times the size of M. These values would be adjusted for different data types (See FIG. 8b).

Having computed the core, the consensus construction may be an optimization problem: we are looking for a candidate sequence of event-sets c such that Q(c, S)=sum(y in C) CP(c,y) is minimized, subject to a "believability" constraint: the events in c cannot be unrealistic. Specifically, in one example, this means that the consensus module 216 may start with an actual episode, and then edits it conservatively, keeping edits such that Q(c,S) improves. The consensus module 216 may use standard optimization techniques (one level backtracking with a greedy algorithm) with two non-standard heuristics described below.

The first non-standard optimization step is when to begin the optimization without inferring the times of individual events by spreading out the times so everything in an event set has precisely the same time, and the event set are kept apart by a fixed delta. After adding or removing events, the consensus module 216 reruns this process. It is only at the end (e.g., once we feel comfortable with the constituent event-groups) that the consensus module 216 adjusts the event times in the consensus by taking the median time of matching events in the episodes in the core set (See FIG. 8c).

In some embodiments, the second non-standard optimization step is a rule in the editing process such that an event cannot be removed if its count would fall below some minimum number, which we take to be the floor of the average of the first and second quartiles for the counts of that event in the core set; this prevents common events from disappearing but does allow us to reduce the number when this improves CP centrality. We also try to add entire groups, but this rarely succeeds as the starting point for consensus tends not to be missing groups—instead groups are missing occasional individual events found in most other event-groups in the core.

In step 320, the prediction module 218 may predict outcomes of novel episodes (i.e., proposed courses of action) using the distance measures discussed herein, and optionally one or more additional distances representing the state of the entity of interest before the episode commences. Each such distance may give rise to a distance matrix between entities. Using a linear combination of one or more such distance matrices, and values of dependent outcome variables, the prediction module 218 constructs a predictor that can predict the values of dependent outcome variables given input of new entity states, episodes, or a combination of both. With such predictions, one may, for example, optimize the entity states, the episodes, or both, with respect to the outcome variable(s) of interest; forecast outcomes based on said inputs; or similar tasks.

Figure 10:
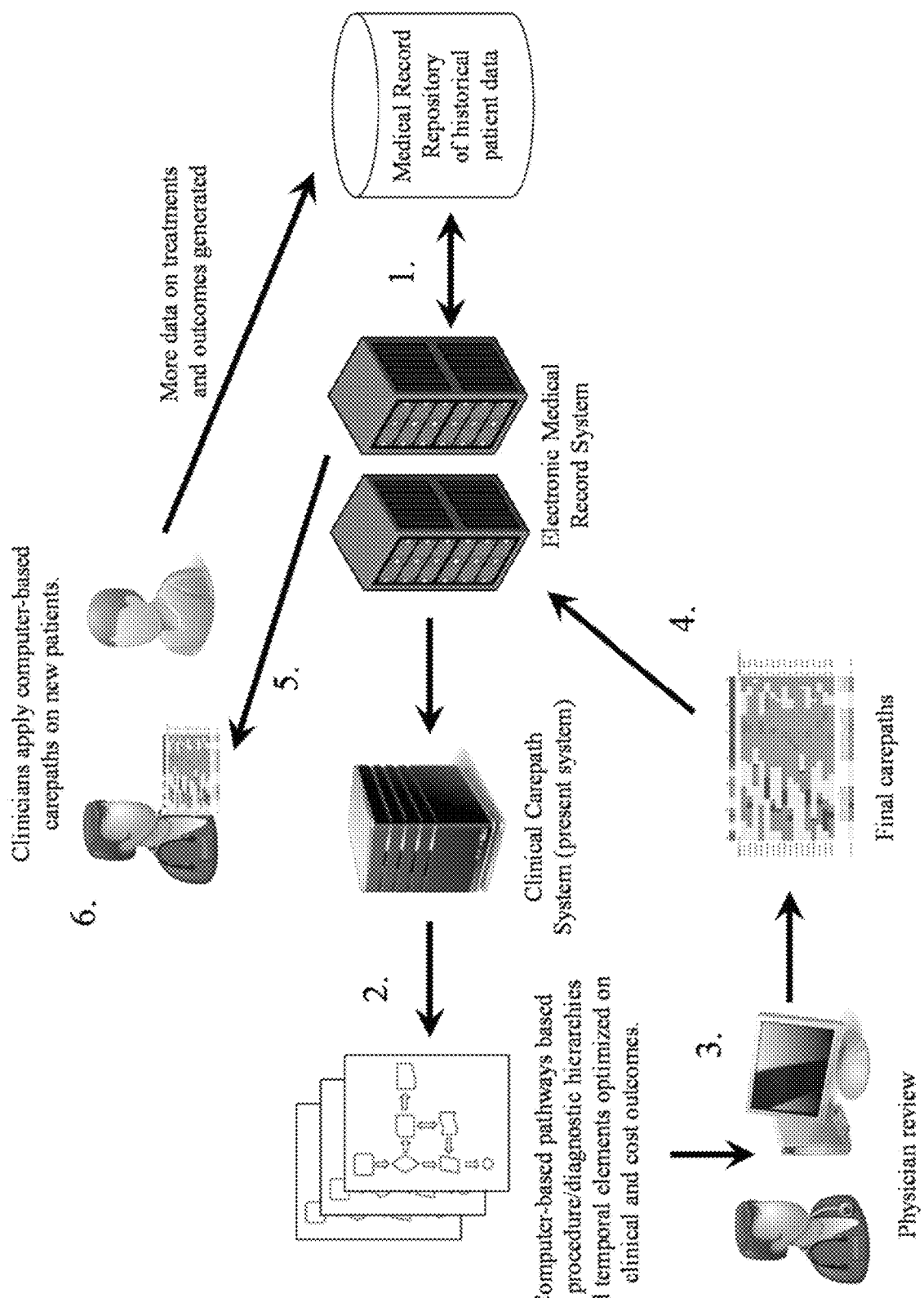
FIG. 10 is a flow diagram of a health care example in some embodiments.

FIG. 10 is a flow diagram of a health care example in some embodiments. In the health care example, a problem being solved is that of perioperative surgical care. In other words, a problem being solved is the determination of which treatment should be provided before and after surgery, inside the hospital, to maximize the chance of a good outcome. Events in this case are various interactions between care providers and patients: lab tests, doctor's orders, and medications administered. Events are considered relative to the time of surgery (the anchor point). In this example, the events are categorized by an ontology present in the data source itself (e.g., an Electronic Medical Record (EMR) database). Event sets map loosely to the notion of order sets: the bundle of one or more actions ordered and/or administered that a care provider specifies during an interaction with the patient.

In this example, episodes are the sequences of such sets over some specified period pre- and post-operatively (e.g., 30 days before and after surgery). Example consensus episodes (in the medical case, "carepaths") are derived using the method(s) described herein, reviewed and modified by physician staff into final form (with support from predictive capabilities), and then built into the EMR system itself. When physicians interact with patients, the EMR system may recommend the carepath to the physician, who the treats the patient and records the treatments along with the outcome. The system then feeds back on itself and continuously improves the carepath over time.

See FIG. 10 for an overview. In step 1, Medical record data repository passes historical patient information to the electronic medical record (EMR) system, which shares this data with the Data-Driven Clinical Carepath System (DDCC) (e.g., the consensus system 106). In step 2, DDCC generates draft clinical carepaths based on clinical outcomes and cost reduction goals. These drafts may be made available to physicians. In step 3, physicians review the draft carepaths and generate the final versions. In step 4, final carepaths are uploaded to the EMR, allowing them to be activated automatically as patients enter the medical system. In step 5, the patient has a new medical encounter, and the clinical carepath is activated depending on diagnosis or procedure ordered.

In a further example, a sequences of event sets are constructed from historical information. As per above, events may be derived from the EMR database, and clustered into sets with a 5 minute timeout. In some embodiments, events are expected to be time stamped to within at least minute-level accuracy, and many events may share a time stamp.

At least one metric on the events may be subsequently learned. Thousands or tens of thousands of event types can be categorized into on the order of 100 high-level categories (e.g. X-rays, analgesics, nursing orders, etc.), from an ontology present in the EMR data. Given this categorization, the metric may be learned from treatments (e.g. all surgical episodes) present in the database, or a subset of that data over some specified time, surgical procedure, hospital, or similar. At least one metric may be derived on the event sets. Event sets may be treated as described above.

Subsequently, Metrics may be assembled on episodes. A modified DTW algorithm described above may be used. In this example, there is a single anchor point, which is the exact start time of the surgical procedure. In some embodiments, only perioperative events (i.e., events that happen outside the surgical ward) are taken into account. Events on opposite sides of the anchors may not be aligned (i.e., incur an enormous alignment cost). Only episodes from the same surgical procedure (e.g. total knee replacement) may be compared, as the goal is to produce a carepath tailored to a particular care interaction.

Consensus sequences (carepaths) may be derived from clusters of episodes. Before cluster construction, the episode population may, if desired, be filtered to provide a more targeted set of treatments. For example, one may wish to construct a carepath for only patients with hypertension, patients in a particular area, for a surgeon that is known to be particularly skilled, etc. After any such filtering and clustering, the clusters may be scored according to a scoring scheme provided by the user. For instance, one might consider large clusters to be better (they provide stronger statistical support). It may also be desirable to score the clusters on factors such as cost to the hospital, length of stay, satisfaction of the patient, or the risk of readmission. Any linear combination of such metadata variables may be used. The cluster with the highest score may be selected for consensus construction, and results may be reported back to the user in the form of a specially constructed interface for viewing, manipulating and exporting proposed carepaths (see FIG. 10). Note that the interface also shows the underlying episodes that constructed the carepath (including the starting point for the optimization step), and any metadata attached to such episodes (such as patient comorbidities, vital statistics, attending physician, etc.).

The method may also provide for a way of interactive predicting what changes in the proposed carepath would do in terms of the outcomes of interest. For each cluster core from which a carepath is generated, a predictor (e.g. a K Nearest Neighbor regressor or classifier) may be parameterized on some outcome of interest (e.g. a quality measure like length of stay in the hospital). The system allows a user (e.g. a physician) to interactively alter the proposed carepath, which triggers a prediction of what the novel carepath would do in terms of the outcome. In this manner, the user may inject domain knowledge into the otherwise automated process, and explore what different tweaks of the auto-generated starting points may improve the downstream results. The user may then save the edited carepath, and/or the computer-generated carepath, into the system and move forward in the implementation process.

Figure 11:
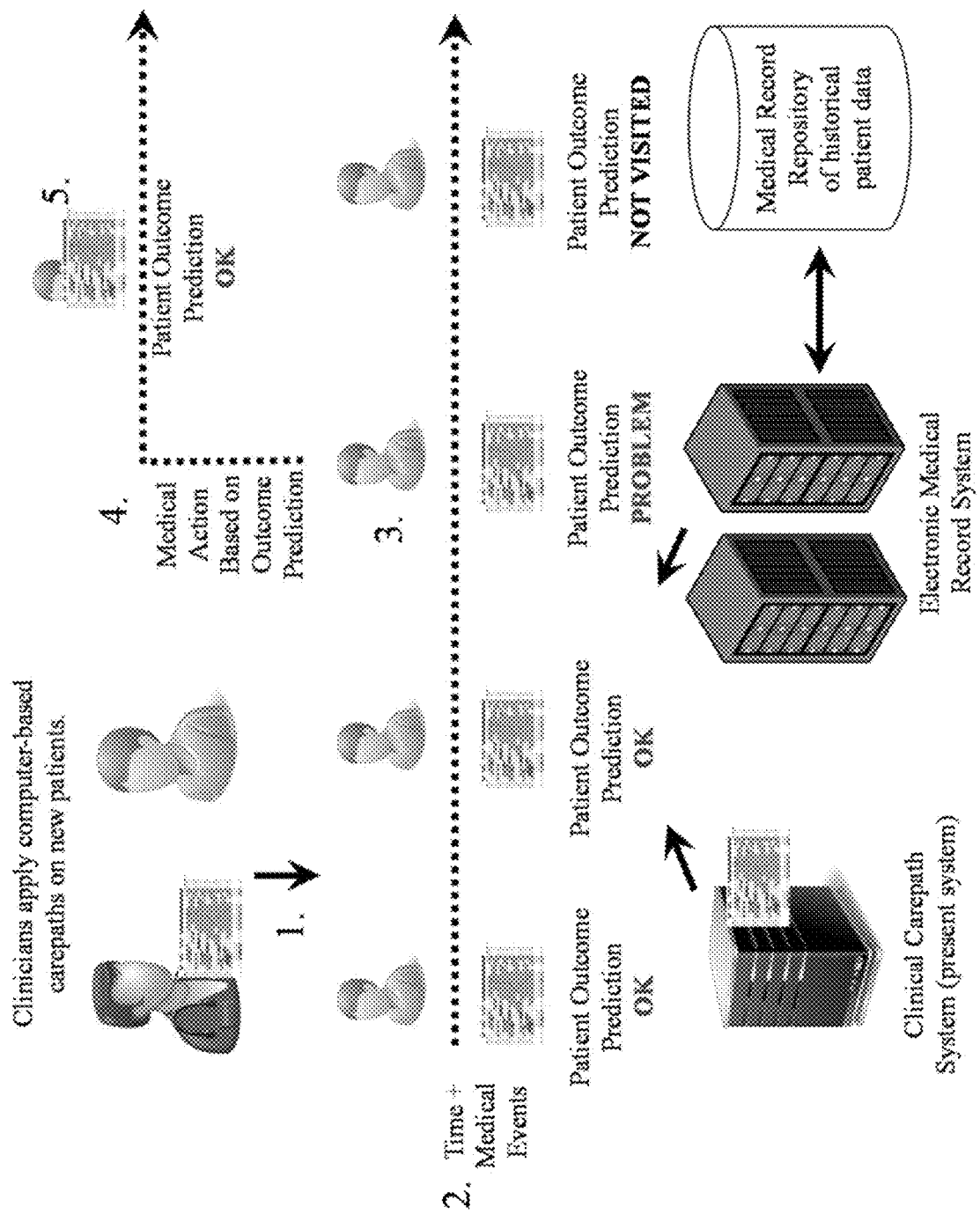
FIG. 11 is another example of the application of some embodiments to health care in some embodiments.

FIG. 11 is another example of the application of some embodiments to health care. In some embodiments, a patient has a new medical encounter, and the clinical carepath is activated depending on diagnosis or procedure ordered. The patient may experience a number of clinical encounters while under treatment. The carepath may be tracked digitally in the EMR to monitor the patient as they progress through the carepath, using predicted outcomes based on patient information from the clinical encounters as a flag for alerting.

Predictions from the digital carepath that suggest poor outcomes based on prior patient encounters are flagged, and the clinician may adjust the patient course of action to improve the predicted outcome. Medical action may be taken based on the change in carepath. Patient outcome prediction is returned to a stable track.

Figure 12:
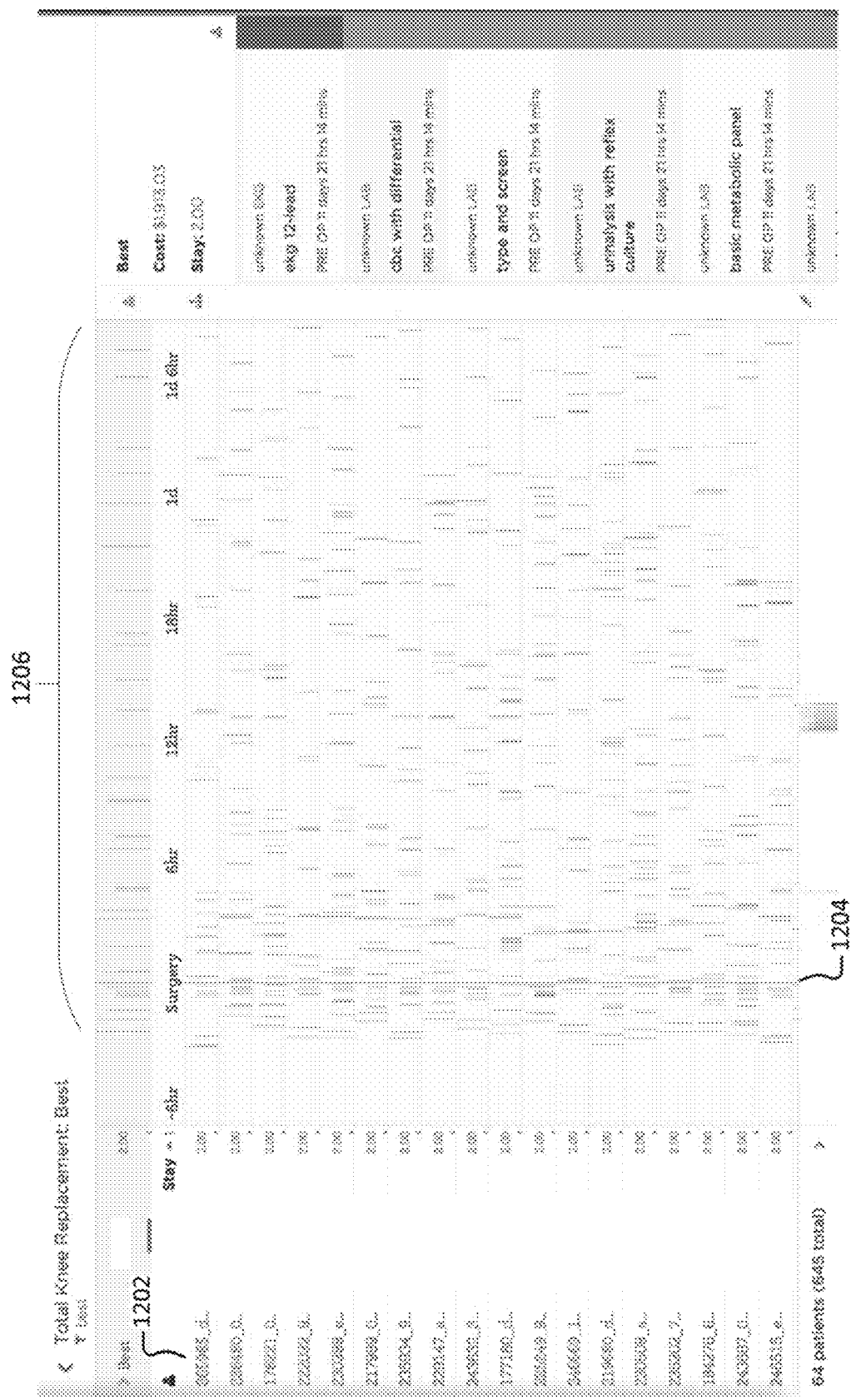
FIG. 12 is an example carepath consensus interface in some embodiments.

FIG. 12 is an example carepath consensus interface in some embodiments. In this example, each patient identifier 1202 (anonymized and fictitious for this example) is associated with a series of events indicated in event sequence 1204. The consensus sequence, in this example, is 1206 at the top of the example carepath consensus interface. The consensus sequence 1206 may indicate the best (e.g., optimal in terms of benefit and/or cost) in view of the historical data associated with each patient identifier 1202. In various embodiments, the example carepath consensus interface and/or the consensus sequence 1206 may be or included in the consensus report.

Figure 13:
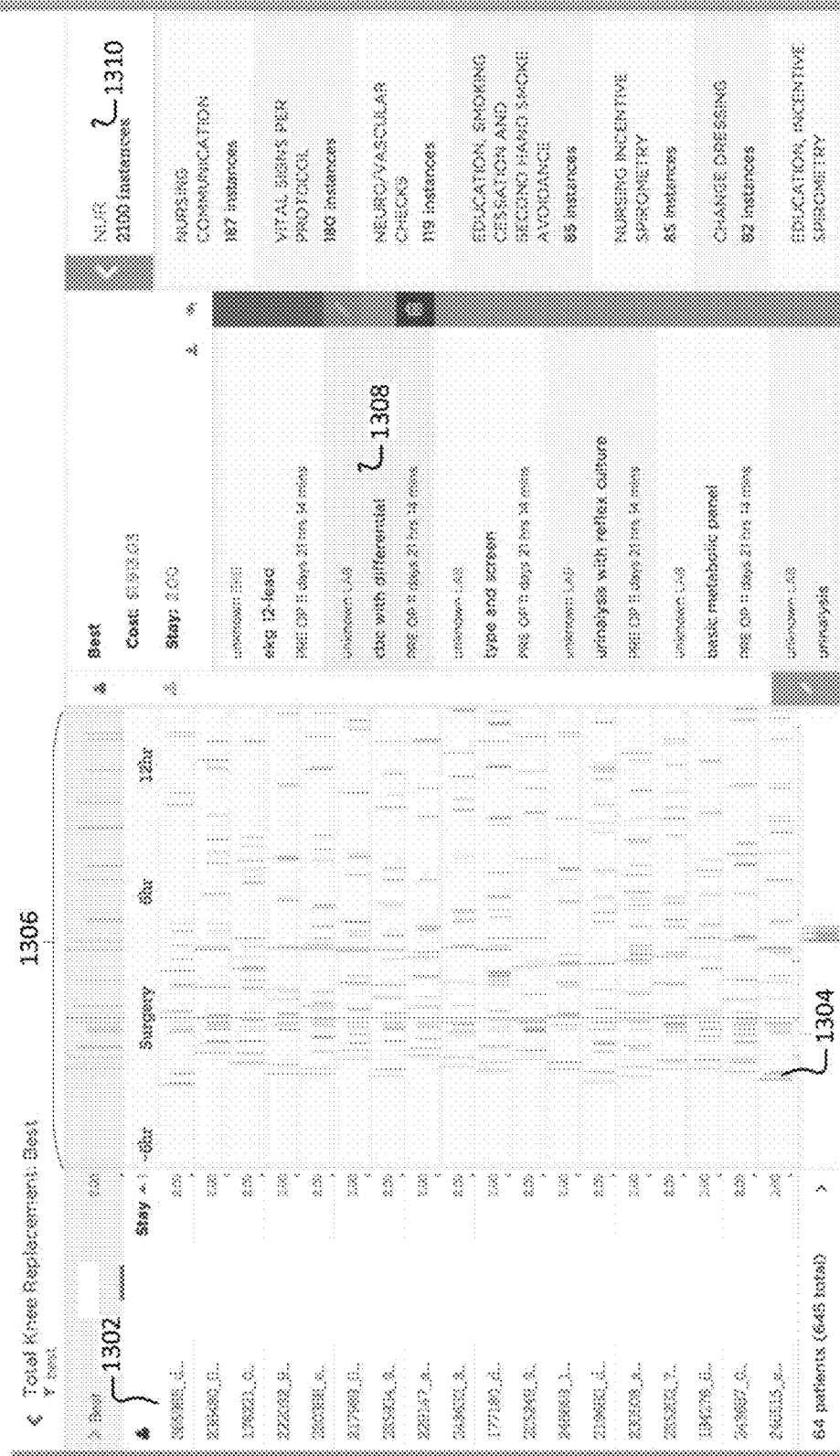
FIG. 13 is an example carepath consensus edit interface in some embodiments

FIG. 13 is an example carepath consensus edit interface in some embodiments. In this example, each patient identifier 1302 (anonymized and fictitious for this example) is associated with a series of events indicated in event sequence 1304. The consensus sequence, in this example, like FIG. 12, is 1306 at the top of the example carepath consensus interface. The consensus sequence 1306 may indicate the best (e.g., optimal in terms of benefit and/or cost) in view of the historical data associated with each patient identifier 1302. In various embodiments, the example carepath consensus interface and/or the consensus sequence 1306 may be or included in the consensus report.

The example carepath consensus edit interface may allow a user (e.g., medical professional) to interact with the patient event information and/or the consensus sequence 1306. In one example, the user may click on a patient or event and view event information 1308 associated with the selection. It will be appreciated that any number of events may be associated with the selection. In this example, the user may select an event associated with the synthetic category "unknown LAB." Activities 1310 that may be associated with an unknown lab may be depicted to allow the user a better understanding of the type of medical procedures that have been performed in the past, outcome information, likelihood of success, relative cost, order of procedures, and/or the like.

In various embodiments, the example carepath consensus edit interface may allow the user to edit the carepath and/or stored historical information (e.g., adding additional patient information). For example, a user (e.g., a medical professional) may add, remove, or edit events in via the editing interface. An updated consensus sequence may be generated and/or provided to the user based on the changes. In some embodiments, a prediction (e.g., regarding cost and/or length of stay) may be provided based, in part, on the changes.

FIGS. 14a-d depict an example of determining a partition based on scoring for autogrouping in some embodiments. In an example, there is a fixed space, S, of finite size. The nature of the space may be relevant only in so far as there is a way of clustering the space and scoring subsets. Referring to a graph G on S indicates a graph whose nodes are a collection of subsets where a node is connected to another node if and only if the two nodes have points in common. A partition includes one or more subsets. Each of the one or more subsets include all of the element(s) of S. For example, partition 1402 is a partition that includes subsets of all elements of S. Subsets 1404a-e include all elements of S. A union of all of the subsets 1404a-e is the partition 1402.

Figure 14A:
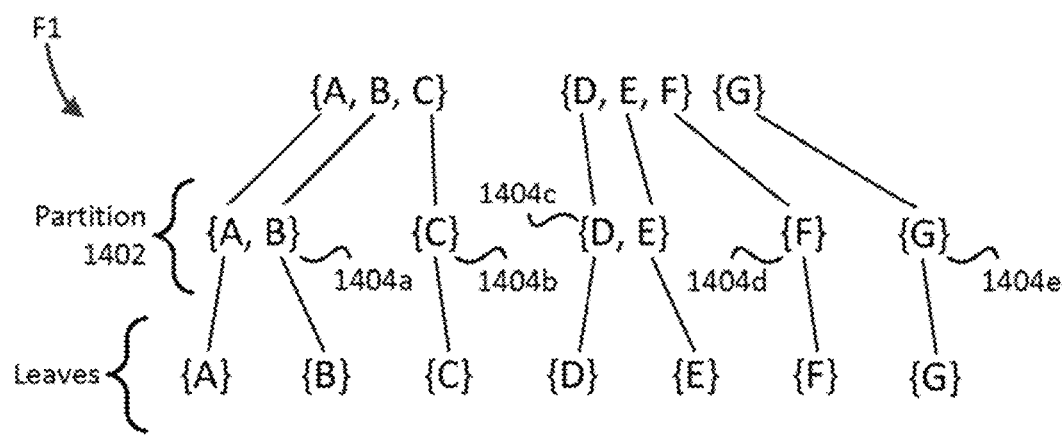
FIGS. 14a-d depict an example of determining a partition based on scoring for autogrouping in some embodiments.
Figure 14B:
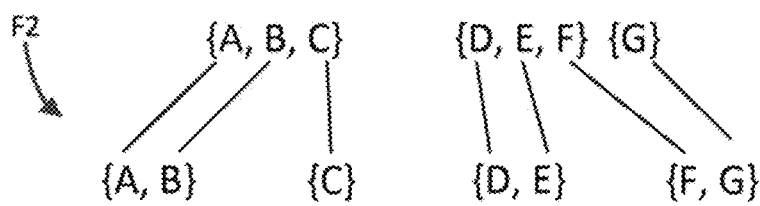
Figure 14C:
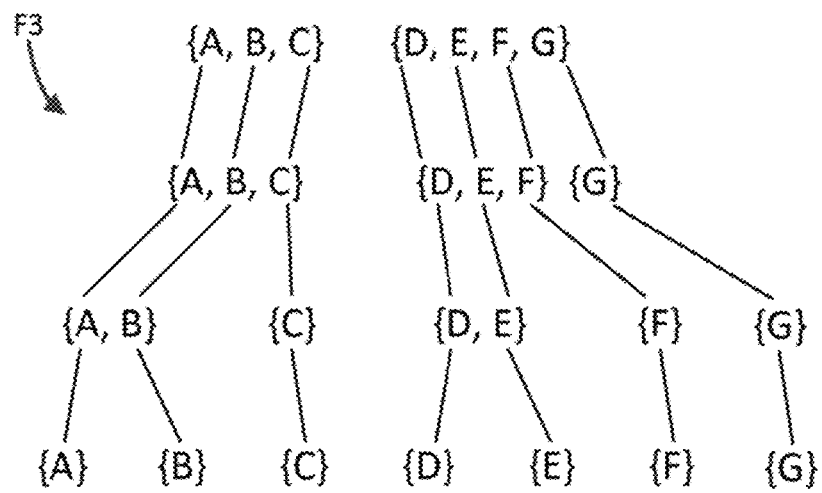

A forest F on S is a graph on S. A forest F is 'atomic' if every leaf in F is a singleton (e.g., a set with one member). FIG. 14a (i.e., F1) is an atomic forest because every leaf in F1 as depicted in FIG. 14a is a singleton. It will be appreciated that FIG. 14b (i.e., F2) is not an atomic forest since every leaf in F2 as depicted in FIG. 14b is not a singleton. For example, F2 includes leaves {A,B}, {D,E}, and {F,G}.

There is a partition R of S (in F1, {a,b,c}, {d,e,f}, {g}), called the roots, such that every set in F is reachable by a unique path from a root. N in F is either a leaf (e.g., a singleton in an atomic forest) or it is connected to nodes which form a partition (e.g., {a,b,c}->{a,b} and {c} in F1) of N. For a non-leaf node N we denote by C(N) the children of N. Notice the children of a leaf, namely C(leaf) is empty. We say that F' extends F if F and F' have the same leaves and every node in F is a node in F'. If the two forests are not equal, then F contains a node which is the union of one or more roots in F'. Example F3 (FIG. 14c) extends F1 (FIG. 14a).

Figure 14D:
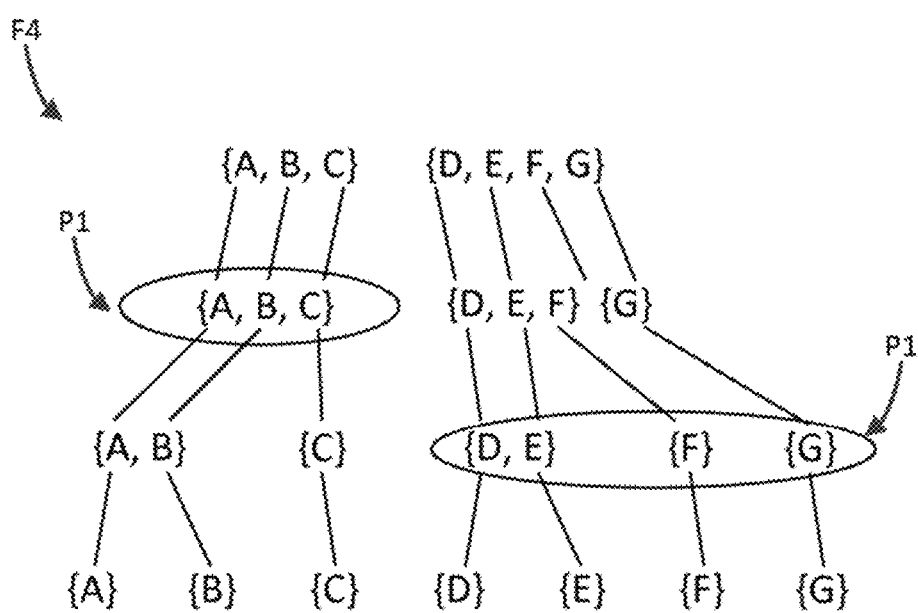

Partition P on S is subordinate to F1 if and only if every element of P is in F1. The circled partition P1 of F4 depicted in FIG. 14d, is an example of a subordinate partition {e.g., {a,b,c}, {d,e}, {f}, and {g}} to F1.

Singletons(S) are denoted as the partition formed by taking {{x}|x in S}. That is, in the example in FIG. 14d, Singletons({a, b, c, d, e, f, g})={{a}, {b}, {c}, {d}, {e}, {f}, {g}}. This is the same as the set of leaves of an atomic forest. Let U(P), where P is any collection of subsets of S, denote the union of all the elements of P. U(Singletons(S))=S.

Partition P on S is coarser than another partition P on S if and only if every element x' in P' is the union of elements x in P. In various embodiments, every partition on S is coarser than Singletons(S), and {S} is coarser than every partition on S. For instance, {{a,b,c}, {d,e,f}, {g}} is a coarser partition than ({a,b}, {c}, {d,e}, {f}, {g}).

Figure 15:
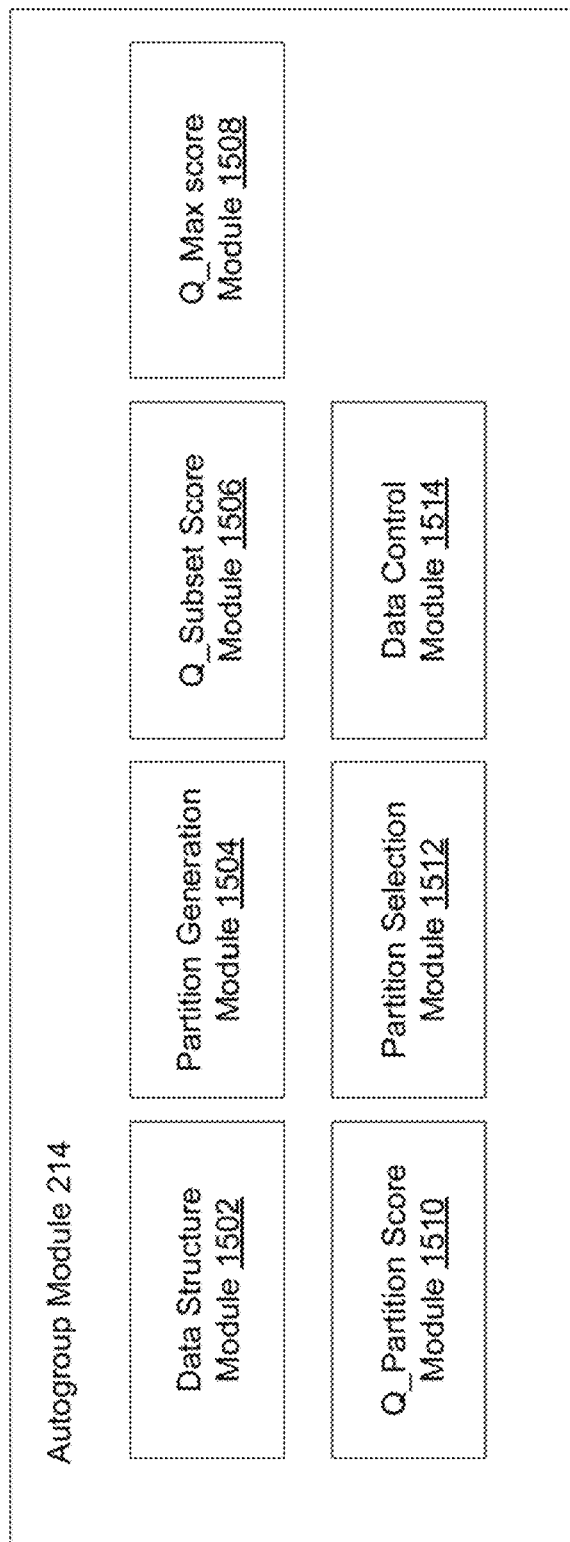
FIG. 15 depicts an example autogroup module in some embodiments.

FIG. 15 depicts an example autogroup module 214 in some embodiments. An autogroup module 214 may comprise a data structure module 1502, a partition generation module 1504, scoring function modules (e.g., a Q_subset score module 1506, a Q_max score module 1508, a Q_partition score module 1510), a partition selection module 1512, and a data control module 1514. Although the scoring function modules are discussed as including three modules, each performing a different scoring function, it will be appreciated that there may be any number of scoring function modules performing any number of scoring functions (e.g., one module performing a single scoring function capable of generating any number or type of scores). For example, the scoring functions may generate and/or maximize metric values of any number of metric functions.

In various embodiments, the data structure module 1502 receives data including a plurality of sets of data. The data may be received from any number of digital devices.

The partition generation module 1504 (e.g., a "clumper") forms a forest F utilizing the plurality of sets of data received by the data structure module 1502. For example, the partition generation module 1504 may generate a first partition of a forest F using the data received by the data structure module 1502. In some embodiments, the first partition may include leaves that are singletons of all elements from the data. In various embodiments, the first partition may include any number of sets of data. The first partition may include leaves for the forest, singletons, roots, sets of plurality of elements, and/or the like.

The partition generation module 1504 may generate the second partition of the forest F using the first partition. For example, the second partition may include at least one union of at least two sets of the first partition. Subsequent partitions may be generated in a similar fashion (e.g., based, at least in part, on including at least one union of at least two sets from the previous partition).

The partition generation module 1504 may generate the entire forest F before scoring partitions (or sets of partitions). For example, the partition generation module 1504 may generate the entire forest F before any or all of the scoring function modules score all or parts of partitions of the forest F.

In some embodiments, the partition generation module 1504 may generate the entire forest F while scoring is performed or in series with partition scoring (e.g., scoring of sets of partitions). For example, the partition generation module 1504 may generate the entire forest F while any or all of the scoring function modules score all or parts of partitions of the forest F. In another example, the partition generation module 1504 may generate one or more partitions of the forest F and then any number of the scoring function modules may score the generated partitions before the partition generation module 1504 generates one or more additional partitions of the forest F.

In various embodiments, the partition generation module 1504 may generate a partition of a forest F based on, at least in part, scores by any number of scoring function modules of previously generated partition(s) (or sets of partition(s)) of the forest F.

It will be appreciated that the partition generation module 1504 may not generate the entire forest F but may rather terminate generating partitions of the forest F before the forest F is completed. The partition generation module 1504 may determine whether to build a new partition of the forest F based on any number of the previously generated partition(s) of the forest F and/or scoring associated with all or parts of previously generated partition(s).

As discussed herein, the partition generation module 1504 may not generate all possible sets of data and/or all possible partitions of the forest F.

It will be appreciated that the partition generation module 1504 may utilize any number of hierarchical clustering techniques with techniques described herein. In one example, data and/or nodes are joined by epsilon (if 2 data subsets or nodes are within distance epsilon of each other then they are joined together). While this example standard technique has traditional limitations ("fixed epsilon") whereby a single epsilon may be unable to break up a space in a preferable manner, by scoring each subset of a partition, we can select subsets across a forest to identify and/or generate a selected partition (e.g., by auto-grouping subsets of a plurality of partitions).

One example of a hierarchical clustering technique, KNN on a finite metric space X is to compute the K nearest neighbors for each point with, for example, K=50. The partition generation module 1504 may start with INITIAL( ) being Singletons(X). Then at each step for 1<=k<=50, the partition generation module 1504 may connect x to y provided x and y are in the symmetric k nearest neighbors of one another. Note that if KNN(P,k) returns P for k<50, the partition generation module 1504 may bump k and try again instead of concluding that P is stable.

Another hierarchical clustering technique embodiment is defined on a weighted graph G (with positive weights) on a point set S. This hierarchical clustering technique is parameterized by a pre-determined real number delta where 1>delta>0. The partition generation module 1504 starts with delta=0 so INITIAL( ) being Singletons(S). For each partition P, we define wt(p,q), for p!=q in P, to be the sum of edge weights between the nodes in the graph which are a part of the subset p and those in the subset q in G, divided by |p|*|q|. The partition generation module 1504 is configured to take a partition P and make a new partition P' by joining all pairs of subsets (a,b) (where a, b are subsets in the partition P) when wt(a,b)>=delta*max(wt(p,q)) where the max is over all pairs of subsets p and q in the partition P.

There are any number of techniques for hierarchical clustering and any of them can be combined with a scoring function that satisfies example constraints on the scoring functions discussed herein.

The autogroup module 214 includes the Q_Subset score module 1506, the Q_Max score module 1508, and the Q_Partition score module 1510 which may utilize three scoring functions, respectively. The Q_Subset score module 1506 calculates a Q_Subset score for subsets of one or more partitions. The Q_Max score module 1508 calculates a Q_Max score based on the Q_Subset score (e.g., calculates a maximum score for a partition based on the Q_Subset score) for the subsets. The Q_Partition score module 1510 calculates a Q_Partition score for two or more partitions of the forest utilizing at least the Q_Subset Score for the subsets.

In various embodiments, the Q_Subset score module 1506 calculates Q_Subset scores (e.g., one for each subset of a partition). A function Q is defined on subsets of the space S and scores the properties which are to be grouped together in the auto-grouping process. For instance, in some embodiments, the Q_Subset score is a modularity score on a graph (so S are the nodes in the graph). The partition selection module 1512 may examine the data structure for a partition of the graph S with maximum modularity score(s).

The second scoring function, the Q_Partition score, may be an extension of the first scoring function Q to be defined on partitions of the space S. If the scoring function Q is defined on subsets of S, it can be extended to a partition function Q_Partition in various ways. One of the simplest ways to extend function Q to partitions is by defining Q_Partition (P) as the sum over p in P of Q(p) (e.g., for a partition P, Q_Partition (P)=sum_{subsets p in P} Q(p)).

In various embodiments, Q_Partition must have the following property: Let P be an arbitrary partition of a subset of S, let p belong to P, and let q be a partition of p. P(q) is defined to be the partition of obtained by replacing p in P with the elements of q. Then, in this example, Q_Partition must have the following property for all P, p, q as described above:

$$QP(P(q)) >= QP(P) \text{ if and only if } QP(q) >= Q(\{p\}) \qquad (1)$$

In some embodiments, function Q does not need to come from a set function in this case. Functions Q_Partition which satisfy property (1) are, by definition, stable partition functions. A class of such functions is described as follows.

Let Q be any real-valued function defined on the set of non-empty subsets of S. Let A(p,q) be any function defined on pairs of non-empty subsets such that p is a subset of q. If:

$$A(p,p)==1 \text{ and } A(p,q)*A(q,r)=A(p,r), \text{ for all legal } p,q,r \qquad (2)$$

then we may extend the set function Q( ) to all partitions P by:

$$QP(P)=\text{sum } A(p,U(P))Q(p) \quad p \text{ in } P \quad (3)$$

Note that all real numbers k, $A(p,q)==(|p|/|q|)^k$ satisfies this property. Moreover, k==0 implies A(p,q)==1.

(1) holds for Q defined in (3). If QP and QP' are stable partition functions, then so is x*QP+y*QP' for x, y>=0. We also refer to stable partition functions on S as "partition scoring functions" for F.

For any scoring function of the form (3), a monotonically increasing function f may be chosen from the real numbers to itself and replace Q by Q'( )=fQ( )). In particular, if f( ) is 'sufficiently invertible' (e.g., A( ) and Q( ) are >=0 and f( ) is invertible on the non-negative reals). QP(P) may be defined by:

$$QP'(P)=f\text{-inverse}(\text{sum } A(p,U(P))f(Q(p))) \quad p \text{ in } P \quad (3')$$

Since f(QP(P)) satisfies (1) and f( ) is monotonically increasing, the QP' in (3') also satisfies (1) and extends Q( ) on subsets of S. Concretely, if A==1 and Q( )>=0 on sets, QP(P) may be defined to be the Euclidean norm of Q( ) on the individual elements of P, and still get a scoring function. Also can use the exponential function for f( ) without requiring Q to be non-negative.

In various embodiments, there may be extreme values under comparisons, using either <= or >=, for a function Q defined on partitions of subsets of S. Since Q may be replaced by −Q if the comparison is <=, it may be assumed without loss of generality that maximal values for Q (i.e., >=) are of interest. Specifically, a method for finding the F-subordinate partition on which Q is maximal, provided Q satisfies a simple property, is disclosed herein.

Given a scoring function Q_Partition on F, we can define a scoring function Q_max( ) to be Q(p) if p is a leaf, and max(Q(p),Qmax(C(p))) if not. One consequence of this definition and requirement (1) on Q_Partition is that the maximal partition of a subset p (that is, the partition V of p for which Qmax(V) is maximal) is either p or the union of the maximal partitions of each element of C(p) (ties may be broken by taking the subset p instead the children).

In various embodiments, the auto-grouping method uses a hierarchical clustering process on S to compute F (i.e., to construct the forest F) and if Q_Partition is a scoring function on the roots R of F, we can find the Q_Max maximal partition of S subordinate to F. As we said above, the intuition here is that joining a scoring function Q( ) with hierarchical clustering provides a principled method for choosing among the partitions for the "Q-maximal partition."

The partition generation module 1504 begins with the original space S and forms a forest F described above. Specifically, in some embodiments, the generation module 1504 takes a partition P and returns a new partition P' which is coarser than P. Note that ({S})={S}. Any partition P such that generation module 1504 (P)=P is called clumper-terminal, and repeated applications must eventually reach a clumper-terminal partition. The sequence Singletons(S), Clumper(Singletons(S)), Clumper(Clumper(Singletons (S))), etc., terminates in a finite number of steps, and the union of all these partitions forms an atomic forest F whose roots are the elements in a C-terminal partition R, which are the roots of F.

One example process utilizing the scoring functions and generating partitions is as follows in the following pseudo-code:

```
P = INITIAL(S) // some initial partition - often Singletons( ), but it
can be anything
F = Tree(P) // node for every subset, remember connections, and have
max slot
              // to hold partition of the node's set which
              has maximal score
for (x in S) { {x}.max = {x} }
BEGIN
    P' = clumper(P)
    if P==P'
        then
            quit
        else
            UPDATE_Qmax(P',P)
END
UPDATE_Qmax(P',P)
    for (p in P') {
        if (!(p in P)) {
            Subset pSubset = AddSubset(p,F);
            if (Q(p) >= QP(C(p)))
                pSubset.maxPartition = p
                pSubset.Qmax = Q(p)
            else
                pSubset.Qmax = QP(C(p))
                pSubset.maxPartition = MAX_UNION(C(p))
        }
    }
MAX_UNION({Ni})
    return the union of Ni.max
```

When this process terminates, the elements of the roots R of F may contain their maximal partitions, the union of which is the best partition in F of S.

The partition selection module 1512 finds a partition subordinate to the forest F that maximizes at least one scoring function. For example, the partition selection module 1512 may select a partition subordinate to the forest F that maximizes the scoring function QP.

In various embodiments, each subset of a partition (as discussed herein) may be associated with its own scores. For example, each subset of a partition may be associated with a different Q_Max score. The partition selection module 1512 may select subsets of unique elements from any number of different partitions of the forest F using the Q_Max score to generate and select a partition.

For example, looking to FIG. 19d, the partition selection module 1512 may select subset {A,B,C} from one partition and subsets {D,E}, {F}, AND {G} from another partition based on a scoring function. The selected subsets may then form (e.g., generate) a new selected partition P1 (e.g., a partition including subsets {A,B,C}, {D,E}, {F}, AND {G}). In this example, the partition selection module 1512 may select the subset {A,B,C} from the first partition utilizing the Q_Max score. In a further example, each subset of all partitions that include any of elements A, B, or C, may be associated with a separate Q_Max score. The maximum Q_Max score of all the sets that include any of the elements of A, B, or C is the subset {A,B,C}. As a result, the partition selection module 1512 selects that subset {A,B,C} in this example.

Similarly, each subset of all partitions that include any of elements D, E, F, or G, may be associated with a separate Q_Max score. The maximum Q_Max scores of all the sets that include any of the elements of D, E, F, or G are the subsets {D,E}, {F, and {G} (i.e., the Q_Max scores associated with subsets {D, E, F, G}}, {D, E, F}, and {G} are not the maximum when compared to the Q_Max scores of subsets {D,E}, {F}, and {G}). As a result, the partition selection module 1512 selects subsets {D,E}, {F}, and {G} in this example.

One example of a scoring function mentioned herein includes a modularity score for weighted graphs on a node set S. In some embodiments, the modularity score of a subset of a graph proportion of edges within a subset, the e's, and the a's which are the proportion of edges which cross the boundaries of the subset. The final score may be e−a^2. In various embodiments, the partition selection module 1512 selects and/or generates a partition by maximizing this score. The modularity partition scorer, QP, may be the sum of the modularity scores on the subsets within that partition.

Another example of a scoring function is a variant of entropy for a set S which has an associated classification: that is, a function cls: S−>{1, 2, . . . , k} (i.e. you have a set and everything has some finite label.) For s subset of S, we define $p\_i(s)=|\{x \text{ in } s:cls(x)==i\}|/|s|$, provided |s|!=0. Then $Q(s)=sum\_\{classes\ i\} (p\_i(s)*log(p\_i(s)))$. The extension of the entropy scorer Q to a partition scorer, QP is given by the extension property (3) where A(p,q)=|p|/|q|. In other words, for a partition P, $QP(P)=sum\_\{p \text{ in } P\} (Q(p)*|p|/|U(P)|)$. Normally one wants to minimize the entropy and the subset scorer here is the negative of the traditional entropy score by maximizing the scoring function.

The data control module 1514 is configured to provide the selected and/or generated partition from the partition selection module 1512. In various embodiments, the data control module 1514 generates a report indicating the selected and/or generated partition from the partition selection module 1512. The report may include, for example, data sets, partitions, subsets, elements, data set identifiers, partition identifiers, subset identifiers, element identifiers, and/or the like. In some embodiments, the report may include a graph (e.g., see FIG. 14) with an indication of selected nodes whose member(s) include data of the selected and/or generated partition from the partition selection module 1512.

Figure 16:
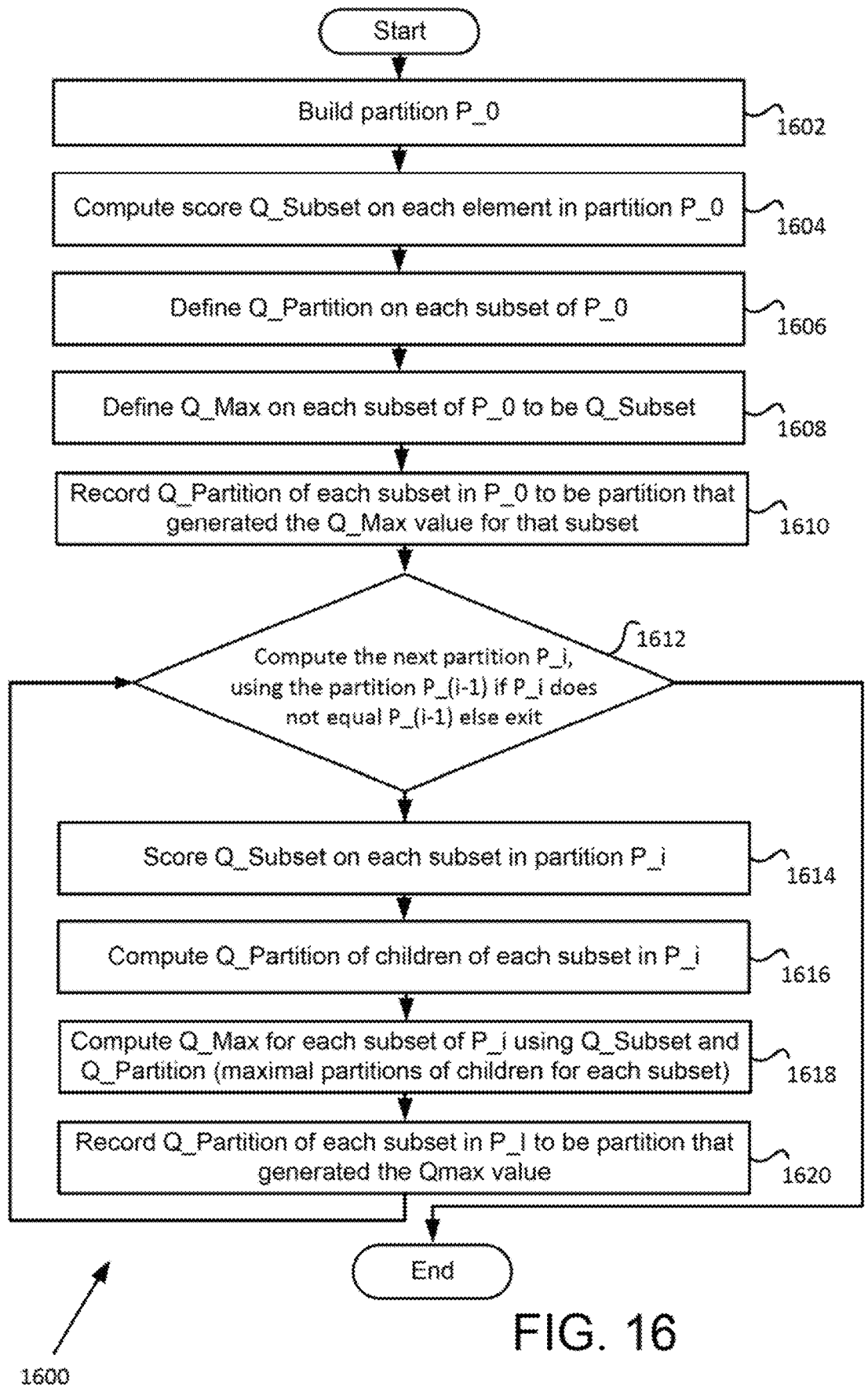
FIG. 16 is an example flowchart for autogrouping in some embodiments.

FIG. 16 is an example flowchart for autogrouping in some embodiments. In this example, the autogroup module 214 receives a set S={A, B, C, D, E, F, G} and performs autogrouping to identify a selected partition of a forest based on S. Non-limiting examples describing at least some of the steps in FIG. 16 will be described using the graph depicted in FIG. 17. The embodiment of the Q_Partition in this example is simply the sum over the subsets of the partition P of the Q_Subset scores on each subset. For example, if P={{A, B, C}, {D}, {E, F}, {G}}, then Q_Partition(P)=Q_Subset({A, B, C})+Q_Subset({D})+Q_Subset({E, F})+Q_Subset({G}).

Figure 17:
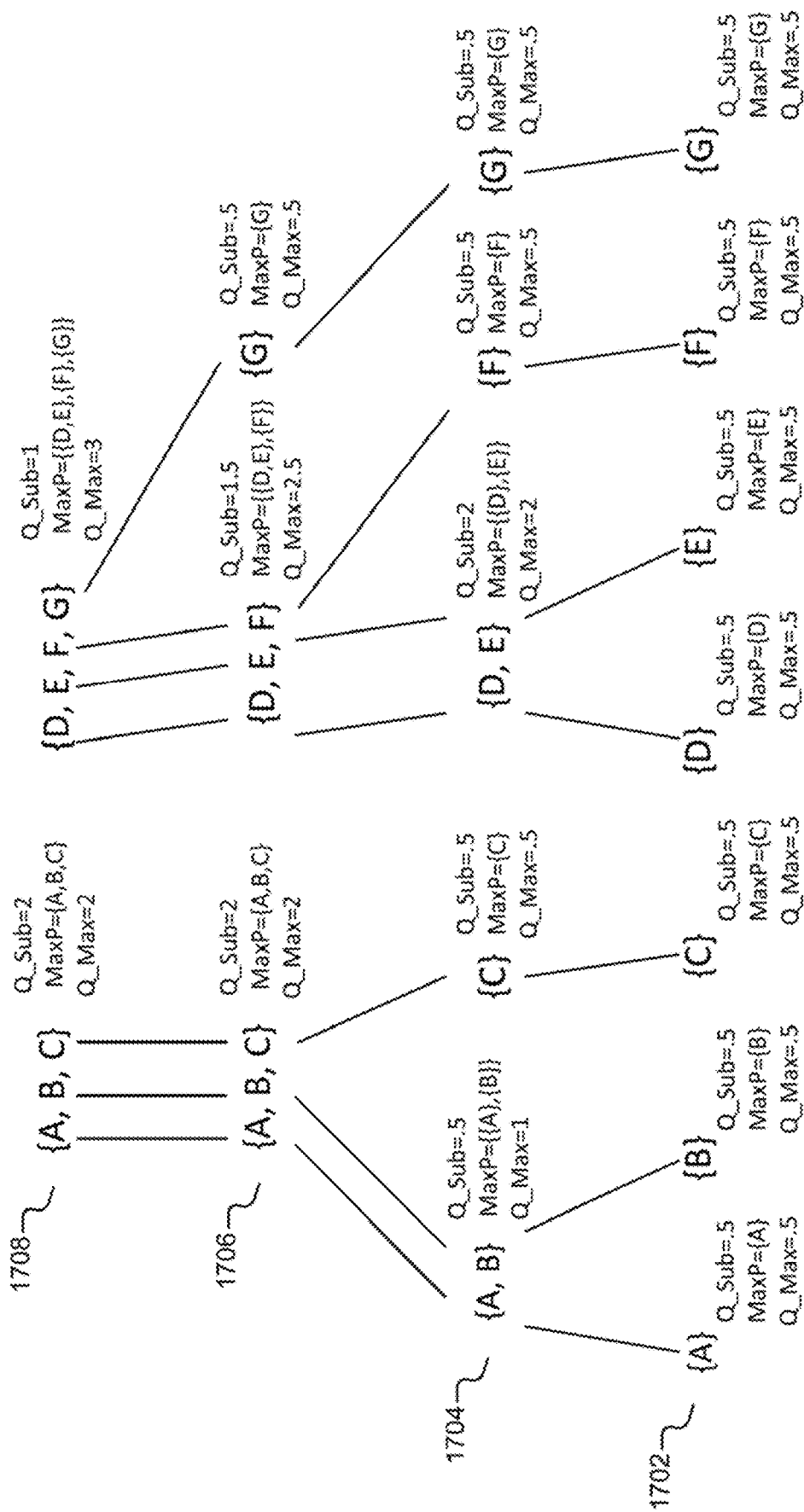
FIG. 17 is an example forest used to describe steps with regard to FIG. 16 in some embodiments.

In step 1602, the data structure module 1502 receives the set S and the partition generation module 1504 generates an initial partition which are the singletons of the set S={A, B, C, D, E, F, G}, namely, P_0={{A}, {B}, {C}, {D}, {E}, {F}, {G}}. This is illustrated in FIG. 17 as the bottom row (1702) of the depicted forest.

In step 1604, the Q_subset score module 1506 computes the Q_Subset score on each subset of the partition P_0. In this example, the Q_subset score module 1506 scores each singleton subset with a value of 0.5. This score is shown in FIG. 17 for each subset of partition 1702 as Q_Sub=0.5.

In step 1606, the Q_partition score module 1510 computes the maximal partition of each subset a of P_0 from the children of the subset a in the constructed forest. Since the subsets a in P_0 have no children in the forest, the maximal partition of the children of the subset a is itself. Namely, for each subset a in P_0, MaximalPartitionChildren(a)=a.

In this example, the Q_partition score module 1510 computes the maximal partition of each subset as itself. This is shown in FIG. 17 for each subset of partition 1702 as MaxP={A} for subset {A}, MaxP={C} for subset {C}, MaxP={D} for subset {D}, MaxP={E} for subset {E}, MaxP={F} for subset {F}, and MaxP={G} for subset {G}.

In step 1608, the Q_max score module 1508 computes Q_Max on each subset of P_0. Recall that since the subsets in P_0 do not have any children, for each subset a in P_0, $$\begin{aligned} Q\_Max(a) &= \max(Q\_Subset(a), \\ &\quad Q\_Partition(MaximalPartitionChildren(a))) \\ &= \max(Q\_Subset(a), Q\_Partition(a)) \\ &= \max(Q\_Subset(a), Q\_Subset(a)) = Q\_Subset(a) \\ &= 0.5 \end{aligned}$$

In this example, the Q_max score module 1508 scores each subset with a value of 0.5. This Q_Max score is shown in FIG. 17 for each subset of partition 1702 as Q_Max=0.5.

In step 1610, we optionally record the maximal partition of each subset a in P_0 to be partition of the subset a that generated the Q_Max for that subset. Thus we record the MaximalPartition(a)=a in this initial partition.

In step 1612, the data structure module 1502 computes the next partition P_1 (the row labeled 1704 in FIG. 17"). Namely, in this example, the data structure module 1502 groups subsets {A} and {B} into the subset {A, B} and subsets {D} and {E} into subset {D, E}. The data structure module 1502 preserved the subsets {C}, {F}, and {G} from the partition P_0 in the partition P_1.

In various embodiments, the data structure module 1502 may determine whether the system ends and/or whether a new partition is to be computed. It will be appreciated that the data structure module 1502 may perform the determination based on any number of ways. In some embodiments, the data structure module 1502 determines if the next generated partition is equal to the previous partition. If the two partitions are equal (e.g., have the same subsets), the method may terminate, otherwise the method may continue to step 1614.

In some embodiments, the data structure module 1502 terminates the method after a predetermined number of partitions are generated, if a predetermined number of roots are found, and/or the like. In various embodiments, the data structure module 1502 may terminate the method if a predetermined number of subsets are present in a computed partition. In another example, the data structure module 1502 may terminate the method after a predetermined period of time, a predetermined period of memory usage, or based on any threshold (e.g., the threshold being calculated based on the amount of data received).

In step 1614, the Q_subset score module 1506 computes the Q_Subset score on each subset of the partition P_1. In this example, the Q_subset score module 1506 computes Q_Subset({A, B})=0.5 and Q_Subset({D,E})=2. As was discussed in the paragraph above describing 1604, Q_Subset of each singleton subset is 0.5 (e.g., the previous Q_Subset score for singleton subsets in 1704 remains unchanged from 1702. These scores are associated with each subset and are visualized in the FIG. 17 as Q_Sub in 1704.

In step 1616, the Q_partition score module 1510 then computes the maximal partition at the children of each subset of P_1. The maximal partition of the children of the subsets {C}, {F}, and {G} are again the original singleton subset. The maximal partition of the children {A, B} is the set including the maximal partitions of the children of {A, B}, namely {{A}, {B}} as depicted in partition 1704 in FIG. 17. Similarly the maximal partition of the children of {D, E} is the set {{D}, {E}} as also depicted in partition 1704 in FIG. 17.

In step 1618, the Q_max score module 1508 computes the Q_Max on each subset of P_1. Recall Q_Max(a)=max (Q_Subset(a), Q_Partition(MaximalPartitionChildren(a)). For the subset {A, B}:

$$Q\_Max(\{A, B\}) = \max(Q\_Subset(\{A, B\}), Q\_Partition(\{\{A\}, \{B\}\}))$$
$$= \max(.5, Q\_Subset(\{A\}) + Q\_Subset(\{B\})$$
$$= \max(0.5, 1)$$
$$= 1$$

For the subset {D, E}:

$$Q\_Max(\{D, E\}) = \max(Q\_Subset(\{D, E\}), Q\_Partition(\{\{D\}, \{E\}\}))$$
$$= \max(2, Q\_Subset(\{D\}) + Q\_Subset(\{E\})$$
$$= \max(2, 1)$$
$$= 2.$$

As displayed in partition 1704 of FIG. 17, Q_Max of {A,B} is 1 and Q_Max of {D,E} is 2. The Q_Max of singletons {C}, {F}, and {G} in partition 1704 remain consistent with the respective subsets in partition 1702. Namely, the Q_Max of each of {C}, {F}, and {G} is 0.5.

In step 1620, we optionally record the maximal partition of each subset a in P_1 that resulted in the Q_Max score. As seen above and in FIG. 17, MaxPartition({A, B})={{A}, {B}} and MaxPartition({D, E})={D, E}.

Now repeat step 1612. The data structure module 1502 computes the next partition P_2, depicted in FIG. 17 as row (partition) 1706. In various embodiments, the data structure module 1502 may determine whether the system ends and/or whether a new partition is to be computed. It will be appreciated that the data structure module 1502 may perform the determination based on any number of ways.

In step 1614, the Q_subset score module 1506 computes the Q_Subset score on each subset of the partition P_2. In this example, the Q_subset score module 1506 computes Q_Subset({A, B, C})=2 and Q_Subset({D, E, F})=1.5. Again, Q_Subset({G})=0.5. These scores are recorded with each subset and are visualized in the FIG. 17 in partition 1706.

In step 1616, the Q_partition score module 1510 computes the maximal partition at the children of each subset of P_2. The maximal partition of the children{G} is the subset {G}. The maximal partition of the children {A, B, C} is the set consisting of the maximal partitions of the children of {A, B, C}, namely {MaxPartition({A,B}), MaxPartition({C})}={{A}, {B}, {C}}. Similarly the maximal partition of the children of {D, E, F} is the set {MaxPartition({D, E}), MaxPartition({F})}={{D, E}, {F}}.

This is shown in FIG. 17 for each subset of partition 1706 as MaxP={A,B,C} for subset {A,B,C}, MaxP={{D,E}, {F}} for subset {D,E,F,}, and MaxP{G} for subset {G}.

In step 1618, the Q_max score module 1508 computes the Q_Max on each subset of P_2. Recall Q_Max(a)=max (Q_Subset(a), Q_Partition(MaximalPartitionChildren(a)). For the subset {A, B, C}:

$$Q\_Max(\{A, B, C\}) = \max(Q\_Subset(\{A, B, C\}),$$
$$Q\_Partition(\{\{A\}, \{B\}, \{C\}\}))$$
$$= \max(2, Q\_Subset(\{A\}) + Q\_Subset(\{B\}) +$$
$$Q\_Subset(\{C\}))$$
$$= \max(2, 1.5)$$
$$= 2$$

For the subset {D, E, F}:

$$Q\_Max(\{D, E, F\}) = \max(Q\_Subset(\{D, E, F\}),$$
$$Q\_Partition(\{\{D, E\}, \{F\}\}))$$
$$= \max(1.5, Q\_Subset(\{D, E\}) +$$
$$Q\_Subset(\{F\})$$
$$= \max(1.5, 2.5)$$
$$= 2.5$$

As displayed in partition 1706 of FIG. 17, Q_Max of {A,B,C} is 2 and Q_Max of {D,E,F} is 2.5 The Q_Max of singleton{G} in partition 1706 remains consistent with the respective subset in partition 1704. Namely, the Q_Max {G} is 0.5.

In step 1620, we optionally record the maximal partition of each subset a in P_2 that resulted in the Q_Max score. As seen above, MaxPartition({A, B, C})={{A, B, C}} and MaxPartition({D, E, F})={{D, E}, {F}}.

Now repeat step 1612. The data structure module 1502 computes the next partition P_3, depicted in FIG. 17 as row (partition) 1708. The data structure module 1502 may determine whether the system ends and/or whether a new partition is to be computed.

In step 1614, the Q_subset score module 1506 computes the Q_Subset score on each subset of the partition P_3. In this example, the Q_subset score module 1506 computes Q_Subset({A, B, C})=2 and Q_Subset({D, E, F, G})=1. These scores are recorded with each subset and are visualized in FIG. 17 in partition 1708.

In step 1616, the Q_partition score module 1510 computes the maximal partition at the children of each subset of P_3. The maximal partition of the children {A, B, C} is the set consisting of the maximal partitions of the children of {A, B, C}, namely {MaxPartition({A,B, C})}={{A, B, C}. Similarly the maximal partition of the children of {D, E, F, G} is the set {MaxPartition({D, E, F}), MaxPartition ({G})}={{D, E}, {F}, {G}}.

This is shown in FIG. 17 for each subset of partition 1708 as MaxP={A,B,C} for subset {A,B,C} and MaxP={{D,E}, {F}, {G}} for subset {D,E,F,G}.

In step 1618, the Q_max score module 1508 computes the Q_Max on each subset of P_3. Recall Q_Max(a)=max (Q_Subset(a), Q_Partition(MaximalPartitionChildren(a)). For the subset {A, B, C}:

$$Q\_Max(\{A, B, C\}) = \max(Q\_Subset(\{A, B, C\}), Q\_Partition(\{A, B, C\}))$$
$$= \max(2, Q\_Subset(\{A, B, C\}))$$
$$= 2$$

For the subset $\{D, E, F, G\}$:

$$Q\_Max(\{D, E, F, G\}) = \max(Q\_Subset(\{D, E, F, G\}), Q\_Partition(\{\{D, E\}, \{F\}, \{G\}\}))$$
$$= \max(1, Q\_Subset(\{D, E\}) + Q\_Subset(\{F\}) + Q\_Subset(\{G\}))$$
$$= \max(1.5, 3)$$
$$= 3$$

As displayed in partition 1708 of FIG. 17, Q_Max of $\{A,B,C\}$ is 2 and Q_Max of $\{D,E,F,G\}$ is 3.

In step 1620, we optionally record the maximal partition of each subset a in P_3 that resulted in the Q_Max score. As seen above, MaxPartition($\{A, B, C\}$)=$\{\{A, B, C\}\}$ and MaxPartition($\{D, E, F, G\}$)=$\{\{D, E\}, \{F\}, \{G\}\}$.

Although not depicted in method 1600, the method may continue. For example, the partition selection module 1512 may identify and/or generate a preferred partition from that maximizes one or more scoring functions. In this example, the preferred partition is the MaxPartition. As discussed immediately above, the maximal partition of each subset in P_3 is As seen above, MaxPartition($\{A, B, C\}$)=$\{\{A, B, C\}\}$ and MaxPartition($\{D, E, F, G\}$)=$\{\{D, E\}, \{F\}, \{G\}\}$. The partition selection module 1512 may identify and/or generate the auto-grouped partition $\{\{A, B, C\}, \{\{D, E\}, \{F\}, \{G\}\}$.

The data control module 1514 may provide the identified and/or generated auto-grouped partition in a report and/or identify the auto-grouped partition in data or a graph.

Figure 18:
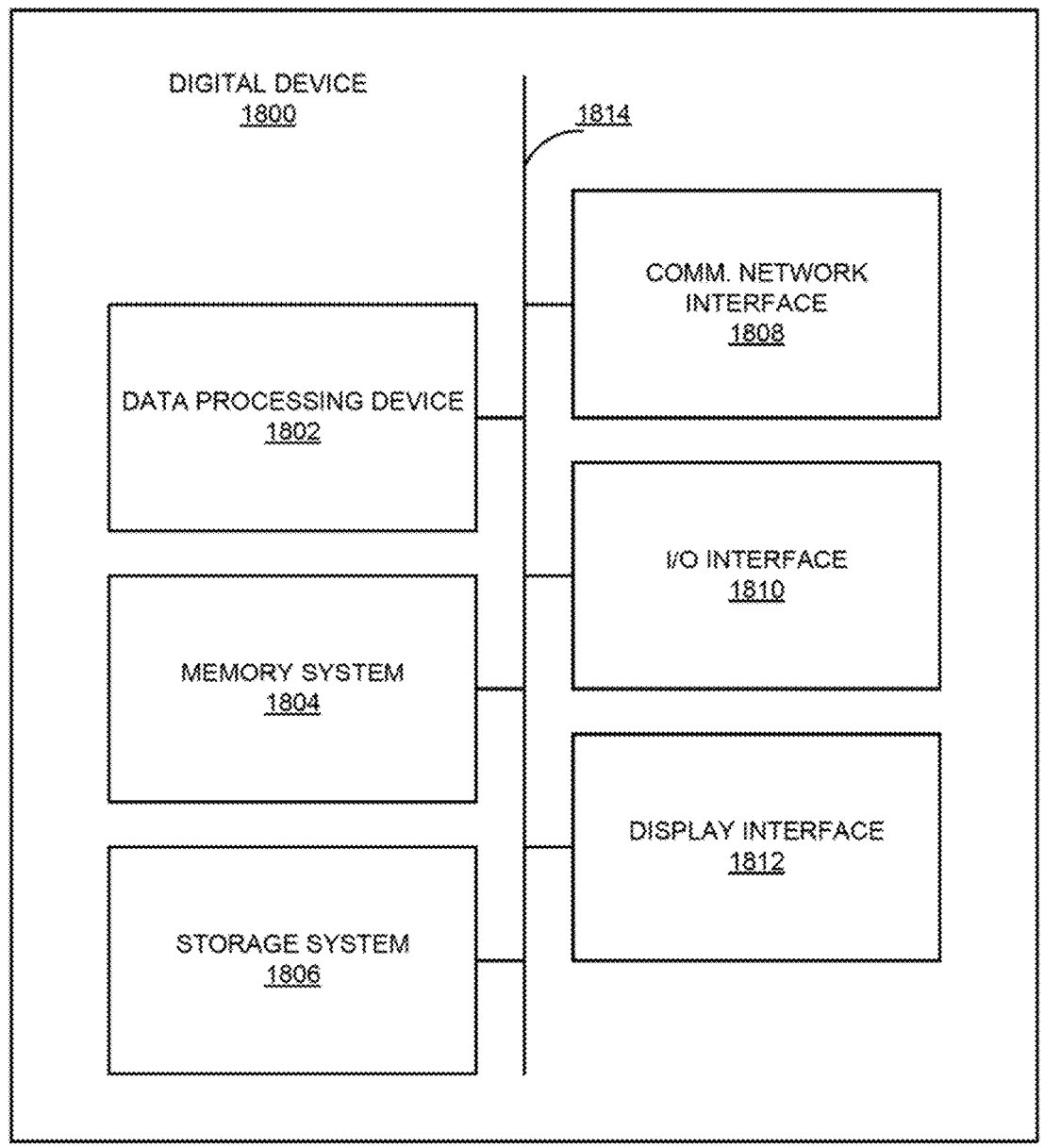
FIG. 18 is a block diagram of an exemplary digital device.

FIG. 18 is a block diagram of an exemplary digital device 1800. The digital device 1800 comprises a data processing device (e.g., a processor) 1802, a memory system 1804, a storage system 1806, a communication network interface 1808, an I/O interface 1810, and a display interface 1812 communicatively coupled to a bus 1814. The processor 1802 is configured to execute executable instructions (e.g., programs). In some embodiments, the processor 1802 comprises circuitry or any processor capable of processing the executable instructions.

The memory system 1804 is any memory configured to store data. Some examples of the memory system 1804 are storage devices, such as RAM or ROM. The memory system 1804 may comprise the cache memory. In various embodiments, data is stored within the memory system 1804. The data within the memory system 1804 may be cleared or ultimately transferred to the storage system 1806.

The storage system 1806 is any storage configured to retrieve and store data. Some examples of the storage system 1806 are flash drives, hard drives, optical drives, and/or magnetic tape. The storage system 1806 may comprise non-transitory media. In some embodiments, the digital device 1800 includes a memory system 1804 in the form of RAM and a storage system 1806 in the form of flash data. Both the memory system 1804 and the storage system 1806 comprise computer readable media which may store instructions or programs that are executable by a computer processor including the processor 1802.

The communication network interface (com. network interface) 1808 may be coupled to a network (e.g., communication network 110) via the link 1816. The communication network interface 1808 may support communication over an Ethernet connection, a serial connection, a parallel connection, or an ATA connection, for example. The communication network interface 1808 may also support wireless communication (e.g., 802.17 a/b/g/n, WiMax). It will be apparent to that the communication network interface 1808 may support many wired and wireless standards.

The optional input/output (I/O) interface 1810 is any device that receives input from the user and output data. The optional display interface 1812 is any device that is configured to output graphics and data to a display. In one example, the display interface 1812 is a graphics adapter. It will be appreciated that not all digital devices 1800 comprise either the I/O interface 1810 or the display interface 1812.

The hardware elements of the digital device 1800 are not limited to those depicted in FIG. 18. A digital device 1800 may comprise more or less hardware elements than those depicted. Further, hardware elements may share functionality and still be within various embodiments described herein. In one example, encoding and/or decoding may be performed by the processor 1802 and/or a co-processor, such as a processor located on a graphics processing unit (GPU).

The above-described functions and components may be comprised of instructions that are stored on a storage medium such as a computer readable medium (e.g., a non-transitory computer readable medium). The instructions may be retrieved and executed by a processor. Some examples of instructions are software, program code, and firmware. Some examples of storage medium are memory devices, tape, disks, integrated circuits, and servers. The instructions are operational when executed by the processor to direct the processor to operate in accord with embodiments of the present invention.

The present invention is described above with reference to exemplary embodiments. Various modifications may be made and other embodiments may be used without departing from the broader scope of the present invention. Therefore, these and other variations upon the exemplary embodiments are intended to be covered by the present invention.

The invention claimed is:

1. A method comprising:
   receiving historical information of past episodes, each past episode including at least one sequence of events taken over a period of time;
   constructing event sets from the historical information each of the event sets including at least one sequence of events;
   categorizing each event from the historical information with general event category labels and synthetic event category labels, at least one of the synthetic event category labels being broader than the at least one general event category label, the at least one of the synthetic event category labels categorizing events which are also categorized by the at least one general event category label and categorizing at least one event not categorized by the at least one general event category label;
   learning an event metric on the events by using the general event category labels and the synthetic event category labels to perform dimensionality reduction to associate a vector with each event and to determine an angle between every two vectors, each general event category label and each synthetic event category label being assigned a separate dimension;

determining an event set metric using distances between each pair of event sets using the event metric;

deriving a sequence metric on the episodes to compute distances between episodes, the sequence metric obtaining a preferred match between two episodes with respect to a cost function describing a weighting for the event set metric;

deriving a subsequence metric on the episodes to compute the distances between episodes, wherein the subsequence metric is a function of the event set metric on subsequences of each episode;

grouping episodes into subgroups based on distances obtained using the sequence metric and the subsequence metric;

for at least one subgroup, generating a consensus sequence by finding a preferred sequence of events with respect to a function of the sequence metric and the subsequence metric between the preferred sequence and the episodes of the at least one subgroup; and generating a report indicating the consensus sequence.

2. The method of claim 1, wherein categorizing each event with general event category labels comprises retrieving an ontology in the historical information and using the ontology to determine the general event category labels.

3. The method of claim 1, wherein the preferred match between two episodes is an optimal match.

4. The method of claim 1, wherein the sequence metric is a carepath (CP) metric.

5. The method of claim 1, wherein the subsequence metric is an event set carepath metric (ESCP) metric.

6. The method of claim 1, wherein the function of the event set metric is a weighted sum.

7. The method of claim 1, wherein each subsequence is defined relative to one or more anchor points in the related episode.

8. The method of claim 1, wherein each event includes a plurality of events.

9. The method of claim 8, wherein an order of the plurality of actions of at least one of the events is not distinguishable.

10. The method of claim 1, wherein constructing event sets from the historical information comprises constructing sets of events separated by no more than a predetermined period of time.

11. The method of claim 1, further comprising filtering the events to remove events that happen infrequently.

12. A non-transitory computer readable medium comprising executable instructions that are executable by a processor to perform a method, the method comprising:

receiving historical information of past episodes, each past episode including at least one sequence of events taken over a period of time;

constructing event sets from the historical information, each of the event sets including at least one sequence of events;

categorizing each event from the historical information with gene-al event category labels and synthetic event category labels, at least one of the synthetic event category labels being broader than the at least one general event category label, the at least one of the synthetic event category labels categorizing events which are also categorized by the at least one general event category label and categorizing at least one event not categorized by the at least one general event category label;

learning an event metric on the events by using the general event category labels and the synthetic event category labels to perform dimensionality reduction to associate a vector with each event and to determine an angle between every two vectors, each general event category label and each synthetic event category label being assigned a separate dimension;

determining an event set metric using distances between each pair of event sets using the event metric;

deriving a sequence metric on the episodes to compute distances between episodes the sequence metric obtaining a preferred match between two episodes with respect to a cost function describing a weighting for the event set metric;

deriving a subsequence metric on the episodes to compute the distances between episodes, wherein the subsequence metric is a function of the event set metric on subsequences of each episode;

grouping episodes into subgroups based on distances obtained using the sequence metric and the subsequence metric;

for at least one subgroup, generating a consensus sequence by finding a preferred sequence of events with respect to a function of the sequence metric and the subsequence metric between the preferred sequence and the episodes of the at least one subgroup: and generating a report indicating the consensus sequence.

13. The computer readable medium of claim 12, wherein categorizing each event with general event category labels comprises retrieving an ontology in the historical information and using the ontology to determine the general event category labels.

14. The computer readable medium of claim 12, wherein the preferred match between two episodes is an optimal match.

15. The computer readable medium of claim 12, wherein the sequence metric is a carepath (CP) metric.

16. The computer readable medium of claim 12, wherein the subsequence metric is an event set carepath metric (ESCP) metric.

17. The computer readable medium of claim 12, wherein the function of the event set metric is a weighted sum.

18. The computer readable medium of claim 12, wherein each subsequence is defined relative to one or more anchor points in the related episode.

19. The computer readable medium of claim 12, wherein each event includes a plurality of events.

20. The computer readable medium of claim 19, wherein an order of the plurality of actions of at least one of the events is not distinguishable.

21. The computer readable medium of claim 12, wherein constructing event sets from the historical information comprises constructing sets of events separated by no more than a predetermined period of time.

22. A system comprising:

at least one processor;

memory comprising instructions to configure at least one of the at least one processor to:

receiving historical information of past episodes, each past episode including at least one sequence of events taken over a period of time;

construct event sets from the historical information, each of the event sets including at least one sequence of events;

categorize each event from the historical information with general event category labels and synthetic event category labels, at least one of the synthetic event category labels being broader than the at least one general event category label, the at least one of the synthetic event category labels categorizing events which are also categorized by the at least one general event category label and categorizing at least one event not categorized by the at least one general event category label;

learn an event metric on the events by using the general event category labels and the synthetic event category labels to perform dimensionality reduction to associate a vector with each event and to determine an angle between every two vectors, each general event category label and each synthetic event category label being assigned a separate dimension;

determine an event set metric using distances between each pair of event sets using the event metric;

derive a sequence metric on the episodes to compute distances between episodes, the sequence metric obtaining a preferred match between two episodes with respect to a cost function describing a weighting for the event set metric;

derive a subsequence metric on the episodes to compute the distances between episodes, wherein the subsequence metric is a function of the event set metric on subsequences of each episode;

group episodes into subgroups based on distances obtained using the sequence metric and the subsequence metric;

for at least one subgroup, generate a consensus sequence by finding a preferred sequence of events with respect to a function of the sequence metric and the subsequence metric between the preferred sequence and the episodes of the at least one subgroup; and generate a report indicating the consensus sequence.

* * * * *